(12) United States Patent
Zhu et al.

(10) Patent No.: US 8,239,006 B2
(45) Date of Patent: Aug. 7, 2012

(54) METHOD AND APPARATUS FOR MEDICAL IMAGING USING NEAR-INFRARED OPTICAL TOMOGRAPHY AND FLUORESCENCE TOMOGRAPHY COMBINED WITH ULTRASOUND

(75) Inventors: Quing Zhu, Mansfield Center, CT (US); Baohong Yuan, Silver Spring, MD (US)

(73) Assignee: The University of Connecticut, Farmington, CT (US)

( * ) Notice: Subject to any disclaimer, the term of this patent is extended or adjusted under 35 U.S.C. 154(b) by 1347 days.

(21) Appl. No.: 11/774,243

(22) Filed: Jul. 6, 2007

(65) Prior Publication Data

US 2008/0058638 A1 Mar. 6, 2008

Related U.S. Application Data

(60) Provisional application No. 60/806,675, filed on Jul. 6, 2006.

(51) Int. Cl.
*A61B 5/00* (2006.01)

(52) U.S. Cl. ........................ 600/475; 600/437; 600/473

(58) Field of Classification Search .................. 600/443, 600/473, 475, 476, 477
See application file for complete search history.

(56) References Cited

U.S. PATENT DOCUMENTS

| | | | |
|---|---|---|---|
| 6,138,045 A | 10/2000 | Kupinski et al. | |
| 6,185,320 B1 | 2/2001 | Bick et al. | |
| 6,264,610 B1 | 7/2001 | Zhu | |
| 6,524,254 B2 | 2/2003 | Erikson | |
| 6,615,063 B1 | 9/2003 | Ntziachristos et al. | |
| 6,690,958 B1 | 2/2004 | Walker et al. | |
| 6,752,763 B2 | 6/2004 | Erikson | |
| 7,620,445 B2 * | 11/2009 | Tsujita | 600/476 |
| 2002/0072677 A1 | 6/2002 | Sevick-Muraca et al. | |
| 2004/0215072 A1 | 10/2004 | Zhu | |
| 2005/0107694 A1 | 5/2005 | Jansen et al. | |

FOREIGN PATENT DOCUMENTS

| | | |
|---|---|---|
| WO | WO03000137 | 1/2003 |
| WO | WO03077744 | 9/2003 |
| WO | WO03055383 | 10/2003 |

OTHER PUBLICATIONS

Huang et al. ("Dual-mesh optical tomography reconstruction method with a depth-correction that uses a priori ultrasound information", Applied Optics, vol. 43, No. 8, Mar. 2004).*

Huang and Zhu, "Dual-Mesh Optical Tomography Reconstruction Method With a Depth Correction That Uses a Priori Ultrasound Information" Applied Optics, vol. 43, No. 8, Mar. 2004, pp. 1654-1662, Optical Society of America.

(Continued)

*Primary Examiner* — Jonathan Cwern
(74) *Attorney, Agent, or Firm* — Cantor Colburn LLP

(57) ABSTRACT

Methods and apparatus for medical imaging using diffusive optical tomography and fluorescent diffusive optical tomography are disclosed. In one embodiment, a method for medical imaging comprises, scanning a tissue volume with near-infrared light to obtain structural parameters, wherein the tissue volume includes a biological entity, scanning the tissue volume with near-infrared light to obtain optical and fluorescence measurements of the scanned volume, segmenting the scanned volume into a first region and a second region, and reconstructing an optical image and a fluorescence image of at least a portion of the scanned volume from the structural parameters and the optical and fluorescence measurements. In another embodiment an apparatus for medical imaging is disclosed.

17 Claims, 14 Drawing Sheets

OTHER PUBLICATIONS

International Search Report dated Dec. 11, 2007 for application No. 2007/015614. All references cited in PCT listed above.

A. H. Hielscher, et al., Image Reconstruction Schemes for Optical Tomography; Engineering in Medicine and Biology Society (1998); 20th Annual International Conference of the IEEE Hong Kong, China on Oct. 29-Nov. 1, 1998 Piscataway, NJ USA. pp. 876-879, vol. 2; XP010320534; ISBN: 0-7803-5164-9.

M. Huang, et al., 2-D NIR Imaging Reconstruction with Ultrasound Guidance, Biomedical Imaging (2002); IEEE International Symposium on Jul. 7-10, 2002, Piscataway, NJ USA. pp. 1031-1034; XP010600770; ISBN: 0-7803-7584-X.

D.N. Ivanov, Iterative Reconstruction Algorithms in Optical Tomography in Frequency Domain Case; Science and Technology (2005), KORUS (2005); The Ninth Russian-Korean International Symposium on Novosibirsk, Russia on Jun. 26-Jul. 2, 2005, Piscataway, NJ, USA. pp. 163-166; XP010836966; ISBN:0-7803-8943-3.

H. Dehghani, et al., Image Reconstruction Strategies Using Dual Modality MRI-NIR Data; Biomedical Imaging: Macro to Nano (2006) IEEE International Symposium on Apr. 6, 2006, Piscataway, NJ, USA. pp. 682-685; XP010912722; ISBN: 0-7803-9576-X.

International Search Report dated Mar. 7, 2008 for App. #PCT/US2007/016390. All references cited in PCT listed above.

Huang et al., "Dual-mesh optical tomography reconstruction method with a depth correction that uses a prior ultrasound information", Applied Optics, vol. 43, No. 8, pp. 1654-1662, Mar. 10, 2004.

Q. Zhu et al., "Imager that combines near-infrared diffusive light and ultrasound", Optics Letters, vol. 24, No. 15, pp. 1050-1052 Aug. 1, 1999.

Danen et al., "Regional Imager for Low-Resolution Functional Imaging of the Brain with Diffusing Near-Infrared Light", Photochemistry and Photobiology, 1998, 67(1): pp. 33-40.

Zhu et al., Imaging tumor angiogenesis by use of combined near-infrared diffusive light and ultrasound, Optics letters, vol. 28 No. 5, pp. 337-339 Mar. 1, 2003.

Chen et al., "Simultaneous near-infrared diffusive light and ultrasound imaging", Applied Optics, vol. 40 No. 34 pp. 6367-6380 Dec. 1, 2001.

Ebers et al., "Thermal Stability of Polyester-Styrene Resin Systems", Industrial and Engineering Chemistry, vol. 42, No. 1, pp. 114-119 Jan. 1950.

Zhu et al. "Ultrasound-Guided Optical Tomographic Imaging of Malignant and Benign Breast Lesions: Initial Clinical Results of 19 Cases" Neoplasia vol. 5 No. 5, pp. 1-11 Jul. 18, 2003.

Yuan et al., "Separately reconstructing the structural and functional parameters of a fluorescent inclusion embedded in a turbid medium"Optics Express vol. 14, No. 16 Aug. 1, 2006.

* cited by examiner

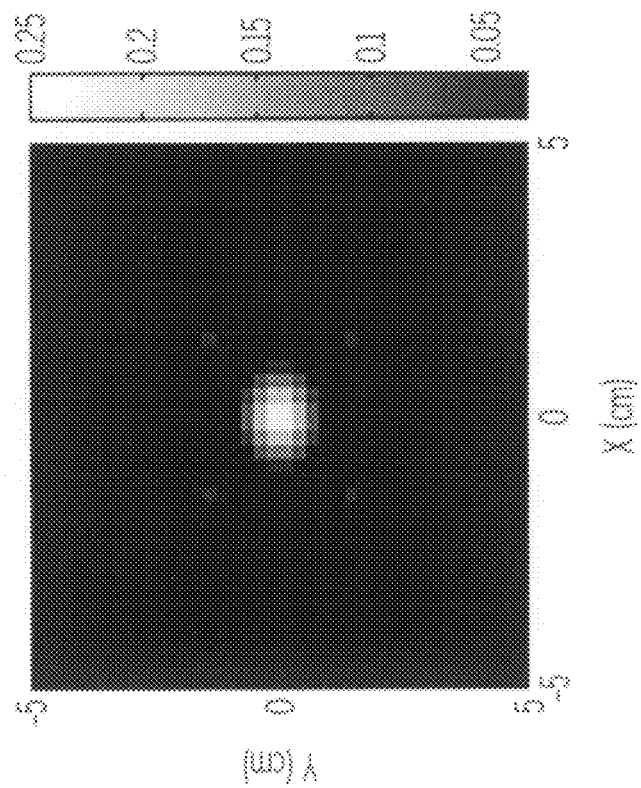
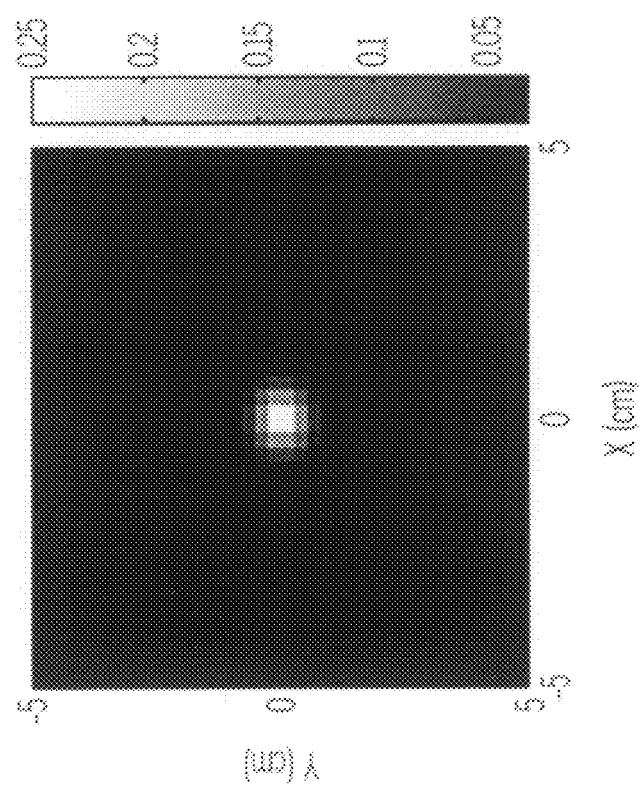
FIG. 18

METHOD AND APPARATUS FOR MEDICAL IMAGING USING NEAR-INFRARED OPTICAL TOMOGRAPHY AND FLUORESCENCE TOMOGRAPHY COMBINED WITH ULTRASOUND

CROSS-REFERENCE TO RELATED APPLICATIONS

This application claims priority to Provisional Application No. 60/806,675 filed Jul. 6, 2006, the entire contents of which are hereby incorporated by reference.

STATEMENT OF FEDERALLY FUNDED RESEARCH

This invention was made with support from the United States Government under contract number R01EB002136 awarded by the National Institutes of Health and contract number W81XWH-04-1-0415 awarded by the Department of Defense. The Government has certain rights in the invention.

TECHNICAL FIELD

This disclosure relates primarily to the field of biological imaging, particularly to medical imaging. More specifically, to medical imaging equipment and methods for medical imaging using combined near-infrared optical tomography, fluorescent tomography and/or ultrasound.

BACKGROUND OF THE INVENTION

Diffusive optical tomography (DOT) is a form of computer-generated tomography wherein near-infrared light (NIR) is directed at a biological object (e.g., a inclusion, tumor, and so forth) and the amount of light transmitted and/or diffused through the object, and/or reflected from the object, is detected and utilized to reconstruct a digital image of the target area (e.g., the object can exhibit a differential in transmission and/or diffusion from surrounding tissues). This method of imaging is of interest for several reasons, for example, differing soft tissues exhibit differing absorption, transmission and/or scattering of near-infrared light. Therefore, DOT is capable of differentiating between soft tissues, wherein alternative tomography methods (e.g., Positron Emission Tomography, Magnetic Resonance Imaging, X-Ray, and so forth) cannot. Another example is that near-infrared light is non-ionizing to bodily tissues, and therefore patients can be subjected to repeated light illumination without harm. This in turn allows physicians to increase the frequency at which they monitor and/or track changes in areas of interest (e.g., inclusions, tumors, and so forth). Yet further, due to differences at which natural chromophores (e.g., oxygen-hemoglobin) adsorb light, optical tomography is capable of supplying functional information such as hemoglobin concentration. For these reasons there is much interest in employing optical tomography for the detection and monitoring of soft tissues, especially in breast cancer applications.

Although diffusive optical tomography is a promising medical imaging technique, DOT imaging methods and DOT apparatus have yet to yield high quality reconstructions of inclusions due to fundamental issues with intense light scattering.

Another method of tomography imaging that is of interest is fluorescent diffusive optical tomography (FDOT). Fluorescent diffusive optical tomography is a form of computer-generated tomography wherein an excitation source (e.g., near-infrared light) is directed at a biological object labeled by a dye fluorophore. Upon excitation of the fluorophore, the wavelength of the excitation source is shifted to a differing wavelength (e.g., a Stokes-shift) as it is emitted by the fluorophore. The emitted light is then detected and utilized to reconstruct a digital image of the target area, which can exhibit a differential in fluorophore concentration from surrounding tissues (e.g., fluorophore take-up). The digital image can be employed to provide functional characteristics about the biological object, such as vascular endothelial growth factor (VEGF). However, FDOT methods have exhibited less than desirable reconstruction accuracy due to imperfect uptake of the fluorophore and background fluorophore noise.

Diffusive optical tomography and fluorescent diffusive optical tomography individually provide benefits over alternative imaging methods. Each of these imaging methods is confronted with challenges that impede widespread acceptance and implementation. However, an optical tomography system capable of providing high quality images of soft tissue to enable physicians to monitor soft tissues with greater frequency, and capable of providing functional characteristics about a portion of biological tissue imaged, would be desirable.

BRIEF DESCRIPTION OF THE INVENTION

Disclosed herein is an apparatus and methods for medical imaging using near-infrared optical tomography, fluorescent tomography, and/or ultrasound.

In one embodiment, a method for medical imaging is disclosed. The method comprises, scanning a tissue volume with near-infrared light to obtain structural parameters, wherein the tissue volume includes a biological entity, scanning the tissue volume with near-infrared light to obtain fluorescence measurements of the scanned volume, segmenting the scanned volume into a first region and a second region, and reconstructing an optical image of at least a portion of the scanned volume from the structural parameters and the fluorescence measurements. In another embodiment an apparatus for medical imaging is disclosed. In an exemplary embodiment, a method for medical imaging using diffusive optical tomography and fluorescent diffusive optical tomography comprises scanning a tissue volume with near-infrared light to obtain structural parameters, wherein the tissue volume includes a biological entity; scanning the tissue volume with near-infrared light to obtain optical and fluorescence measurements of the scanned volume; segmenting the scanned volume into a first region and a second region; and, reconstructing an optical image and a fluorescence image of the scanned volume from the structural parameters and the optical and fluorescence measurements; the reconstructing comprising obtaining structural information and/or functional information about the biological entity contained in the scanned volume; using a model to obtain theoretically calculated data for the structural information and/or the functional information; comparing the theoretically calculated data with experimentally measured data to obtain an objective function; and accepting the theoretically calculated data if the objective function lies within an acceptable limit.

In another embodiment, a method for medical imaging using diffusive optical tomography and fluorescent diffusive optical tomography is disclosed. The method comprises, scanning a tissue volume with near-infrared light to obtain structural parameters, wherein the tissue volume includes an inclusion, scanning the tissue volume with near-infrared light to obtain fluorescence measurements of the scanned volume, segmenting the scanned volume into an inclusion region and a background region, and reconstructing an optical image of at least a portion of the scanned volume from the structural parameters and the fluorescence measurements.

In another embodiment, an apparatus for medical imaging is disclosed. The apparatus comprises a probe comprising an emitter and a detector, a source circuit connected in operational communication the emitter, a detector circuit connected in operational communication to the detector, a central processing unit connected to the source circuit and the detector circuit, a display operably connected to the central processing unit, and wherein the central processing unit is capable of processing information to provide diffusive optical tomography and fluorescent diffusive optical tomography.

In yet another embodiment, an apparatus for biological imaging is disclosed. The apparatus comprises a probe comprising an emitter and a detector, a source circuit connected in operational communication to the emitter, a detector circuit connected in operational communication to the detector, a central processing unit connected to the source circuit and the detector circuit, a display operably connected to the central processing unit, and wherein the apparatus is capable of diffusive optical tomography and fluorescent diffusive optical tomography The above described and other features are exemplified by the following figures and detailed description.

BRIEF DESCRIPTION OF THE DRAWINGS

Refer now to the figures, which are exemplary embodiments, and wherein the like elements are numbered alike.

FIG. 18 is a photograph depicting reconstructed images in X-Y plane of the target (X=Y=0.0 and Z=0.75 cm) using the fine-tuned optical imaging method. #1 and #2 represent the first slice with 0.5 cm in depth and the second slice with 1.0 cm in depth. The boundary is an absorbing boundary.

DETAILED DESCRIPTION OF THE INVENTION

Figure 1:
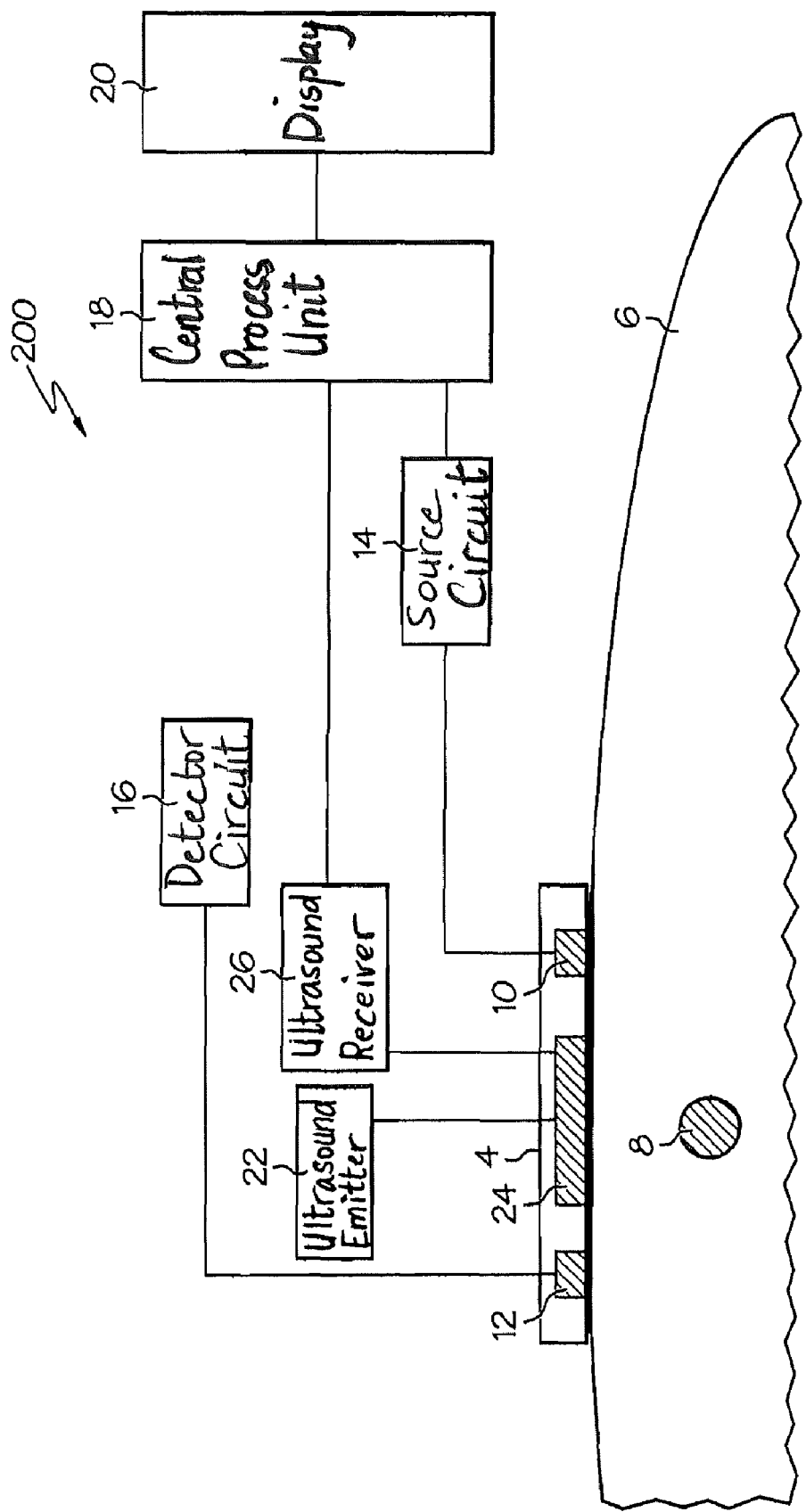
FIG. 1 is a simplified block diagram of an imaging system.

It is to be noted that as used herein, the terms "first," "second," and the like do not denote any order or importance, but rather are used to distinguish one element from another, and the terms "the", "a" and "an" do not denote a limitation of quantity, but rather denote the presence of at least one of the referenced item. Furthermore, all ranges disclosed herein are inclusive of the endpoints and independently combinable Disclosed herein is a medical imaging apparatus and methods for medical imaging wherein diffusive optical tomography (DOT) and fluorescent diffusive optical tomography (FDOT) are employed. In one embodiment, the DOT can be employed in conjunction with the FDOT and further in conjunction with ultrasound, xrays, photoacoustic techniques and/or magnetic resonance imaging. In another exemplary embodiment, the DOT can be employed in conjunction with the FDOT and further in conjunction with ultrasound. The images can be enhanced using one or more of three algorithms provided below. The apparatus and methods yield structural information (e.g., position in X, Y, Z coordinates, radius, and so forth) as well as functional information (e.g., fluorophore concentration and hemoglobin concentration) of an absorbing and fluorescing inclusion within a turbid medium (e.g., soft tissue).

Diffuse optical tomography (DOT) in the near infrared region (NIR) provides a unique approach for functional based diagnostic imaging. However, the intense light scattering in tissue produced by the DOT dominates the NIR light propagation and makes three-dimensional localization of lesions and accurate quantification of lesion optical properties difficult. Optical tomography guided by co-registered ultrasound (US), magnetic resonance imaging (MRI), photoacoustic techniques or x-ray, has a great potential to overcome lesion location uncertainty and to improve light quantification accuracy.

In this co-registration approach, a region of interest (ROI) can be chosen from a non-optical modality ultrasound or MRI, or photoacoustic technique, or x-ray to guide DOT on image reconstruction. However, an accurate lesion delineation for DOT from a non-optical modality is difficult due to different contrast mechanisms. Regions of suspicious lesions seen by optical methods could potentially improve the accuracy of reconstructed optical properties. Described herein is a method that can optically fine tune the lesions seen by ultrasound, photoacoustic techniques, MRI or x-rays and then reconstruct lesion optical properties, such as optical absorption, hemoglobin concentration and fluorescence concentration.

In one embodiment, DOT may be used in combination with FDOT and the first and/or third algorithm. In another embodiment, ultrasound may be used in combination with either DOT and/or FDOT and the first, second and/or third algorithms. In general, when ultrasound is used in conjunction with DOT and/or FDOT, it is desirable to use at least the second algorithm to enhance the images. The ultrasound transducer provides information about the size and location of a fluorescence target (e.g., a fluorescent dye that is preferentially absorbed into a tumor), while the near infra-red sources provide excitation wavelength $\lambda_1$ to illuminate the target, which in turn absorbs the excitation light and generates the fluorescence signals $\lambda_2$. As noted above, the ultrasound information may be substituted with or enhanced with xrays, MRI or photoacoustic techniques.

At the outset, it is to be understood that the term inclusion is to be interpreted as any tissue(s), biological mass(es), biological entity(ies), and/or foreign object(s) that can be differentiated from surrounding tissue(s), biological mass(es), and/or biological entity(ies), using diffusive optical tomography and/or fluorescent diffusive optical tomography. For example, an inclusion can be a tumor that is disposed within soft tissues, such as a tumor within a female breast, wherein the tumor (e.g., comprising epithelial tissues, masenchymal tissues, and so forth) exhibits dissimilar optical diffusion and fluorophore concentration characteristics from surrounding tissues. Also, the term inclusion as used herein can be used interchangeably with the terms biological entity and target. Further, the term structural information refers to any information gathered or determined with respect to the structure, or physical shape, of an inclusion, such as position (e.g., X, Y, Z coordinates), diameter, mass, volume, shape (e.g., circular, elliptical, and so forth), and so forth. Lastly, the term functional information is to be interpreted as any information gathered or determined that can be employed by a physician, operator, or one skilled in the art, to determine additional characteristics about the inclusion.

Referring now to FIG. 1, an exemplary simplified block diagram of an imaging system 200 is illustrated, wherein the imaging system 200 comprises a probe 4 that can be disposed on bodily tissue 6 to image an inclusion 8 therein. The probe 4 comprises a first emitter 10 and a first detector 12, wherein the first emitter 10 is connected in operational communication to a source circuit 14 and an ultrasound emitter 22, and the first detector 12 is connected in operational communication to a detector circuit 16 and an ultrasound receiver 26. The source circuit 14 and detector circuit 16 are operably connected to a central processing unit 18 (hereinafter referred to as CPU 18), which is operably connected to a display 20 on which an image of the inclusion 8 can be generated. The CPU 18 is capable of controlling the operation of the imaging system 200. The probe also comprises a second emitter 24 for emitting and collecting ultrasonic energy into the body tissue 6.

Figure 2:
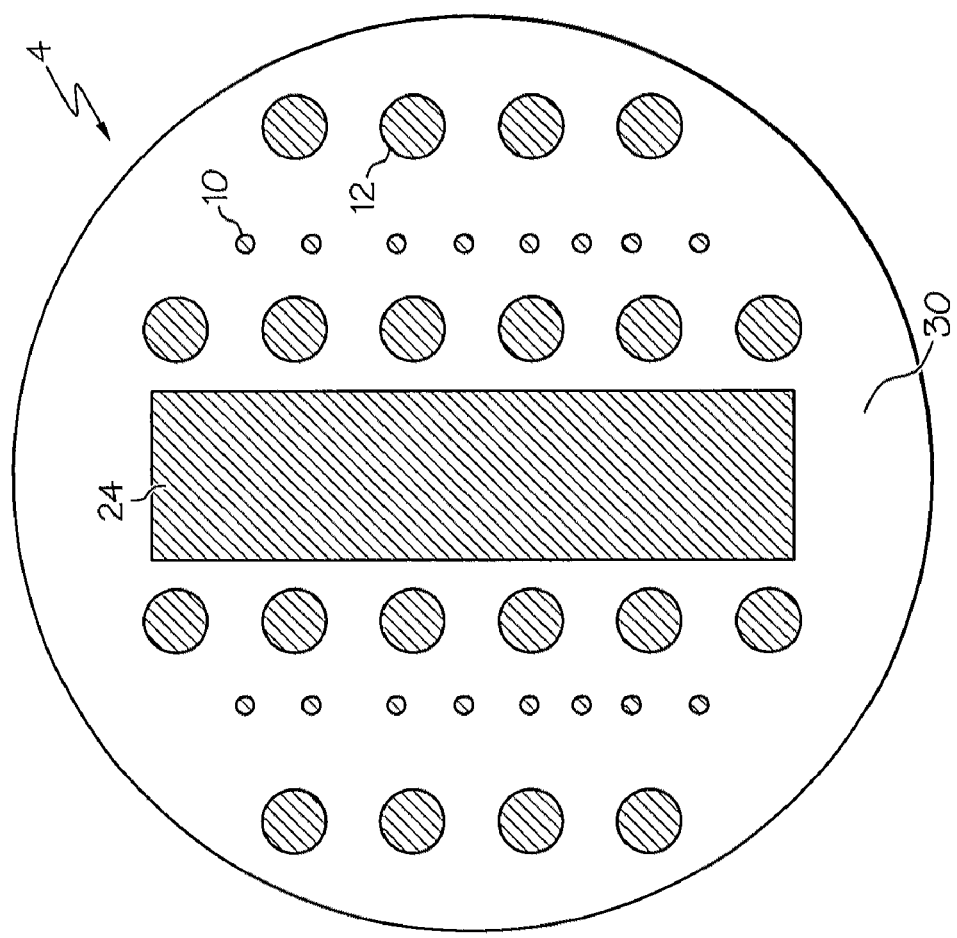
FIG. 2 is an illustration of the front of a probe, which comprising a plurality of emitters and detectors.

FIG. 2 illustrates a front view of the probe 4 having a plurality of first emitters 10 and first detectors 12 disposed on a faceplate 30. The FIG. 2 also depicts a single second emitter (e.g., an ultrasound transducer or array) for emitting and collecting ultrasonic energy into the body tissue. The first emitters 10 are capable of emitting radiation, such as near-ultraviolet light. The first detectors 12 are capable of detecting radiation emitted by the emitters 10 and fluorescence within the target area (e.g., tissue 6 and inclusion 8).

Any number of first emitters 10 and first detectors 12 can be employed to perform the imaging function. In an exemplary embodiment, the probe 4 can comprise about 1 to about 30 first emitters, specifically about 2 to about 20 first emitters and more specifically about 5 to about 10 first emitters. A preferred number of first emitters in the probe 4 is about 9. In another exemplary embodiment, the probe 4 can comprise about 1 to about 30 first detectors, specifically about 2 to about 20 first detectors and more specifically about 5 to about 10 first detectors. A preferred number of first detectors in the probe 4 is about 10. It is noted however that as the number of first emitters 10 and/or first detectors 12 increases, the imaging time (e.g., the time elapsed before radiation received by a detector can be processed and reconstructed into an image and displayed on display 20 by CPU 18) can increase due to the additional information to be processed by the CPU 18.

The first emitters 10 and the first detectors 12 are generally disposed on the surface of the faceplate 30 so that they are in close proximity to the tissue 6 being imaged. The first emitters 10 and first detectors 12 can be disposed in any configuration, thereby allowing the imaging volume to be expanded or localized based on the number and/or spacing of first emitters 10 and first detectors 12.

The probe 4 can also have a plurality of second emitters 24. In an exemplary embodiment, the second emitter is an ultrasound transducer. In one embodiment, the ultrasound transducer is an ultrasound array. It will be recognized that any ultrasound array can be used in the probe 4. For example, the ultrasound array can be 1-dimensional, 2-dimensional, 1.5-dimensional or 1.75-dimensional. In an exemplary embodiment, the probe 4 can have about 1 to about 10 ultrasound transducers. A preferred number of ultrasound transducers is 1. In the present embodiment a 1-dimensional array is used.

The specific shape of the probe 4 and/or faceplate 30 is desirably configured to be an ergonomic design that is suited to traverse across the tissue 6 of a patient without causing discomfort to the patient (e.g., the faceplate 30 can comprise rounded edges, a smooth surface, and so forth). In addition, the probe 4 can be configured such that it can be hand-held by an operator. While the exemplary depiction of the probe 4 in the FIG. 2 shows a circular cross-sectional area, the cross-sectional area can have a geometry that is square, rectangular, triangular or polygonal. In addition, it is further envisioned the probe 4 can be releasably secured to the conduit (e.g., fiber optic cables, wires, and so forth) that connects the probe 4 in operable communication with the source circuit 14 and detector circuit 16.

It is desirable for the surface of the probe 4 to be manufactured from an organic polymer, preferably one that is flexible at room temperature, so that it can be used to accommodate the contours of a body whose tissue is under observation. The organic polymer can comprise a wide variety of thermoplastic resins, blend of thermoplastic resins, thermosetting resins, or blends of thermoplastic resins with thermosetting resins. The organic polymer may also be a blend of polymers, copolymers, terpolymers, or combinations comprising at least one of the foregoing organic polymers. The organic polymer can also be an oligomer, a homopolymer, a copolymer, a block copolymer, an alternating block copolymer, a random polymer, a random copolymer, a random block copolymer, a graft copolymer, a star block copolymer, a dendrimer, or the like, or a combination comprising at last one of the foregoing organic polymers. Exemplary organic polymers for use in the probe 4 are elastomers that have glass transition temperatures below room temperature.

Examples of the organic polymer are polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, fluorinated ethylene propylene, perfluoroalkoxyethylene, polychlorotrifluoroethylene, polyvinylidene fluoride, or the like, or a combination comprising at least one of the foregoing organic polymers.

Examples of blends of thermoplastic resins include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleic-anhydride/acrylonitrile-butadiene-styrene, polyether etherketone/polyethersulfone, polyether etherketone/polyetherimide polyethylene/nylon, polyethylene/polyacetal, or the like.

Examples of thermosetting resins include polyurethane, natural rubber, synthetic rubber, epoxy, phenolic, polyesters, polyamides, polysiloxanes, or the like, or a combination comprising at least one of the foregoing thermosetting resins. Blends of thermoset resins as well as blends of thermoplastic resins with thermosets can be utilized. An exemplary thermosetting resin is polydimethylsiloxane (PDMS).

Figure 3:
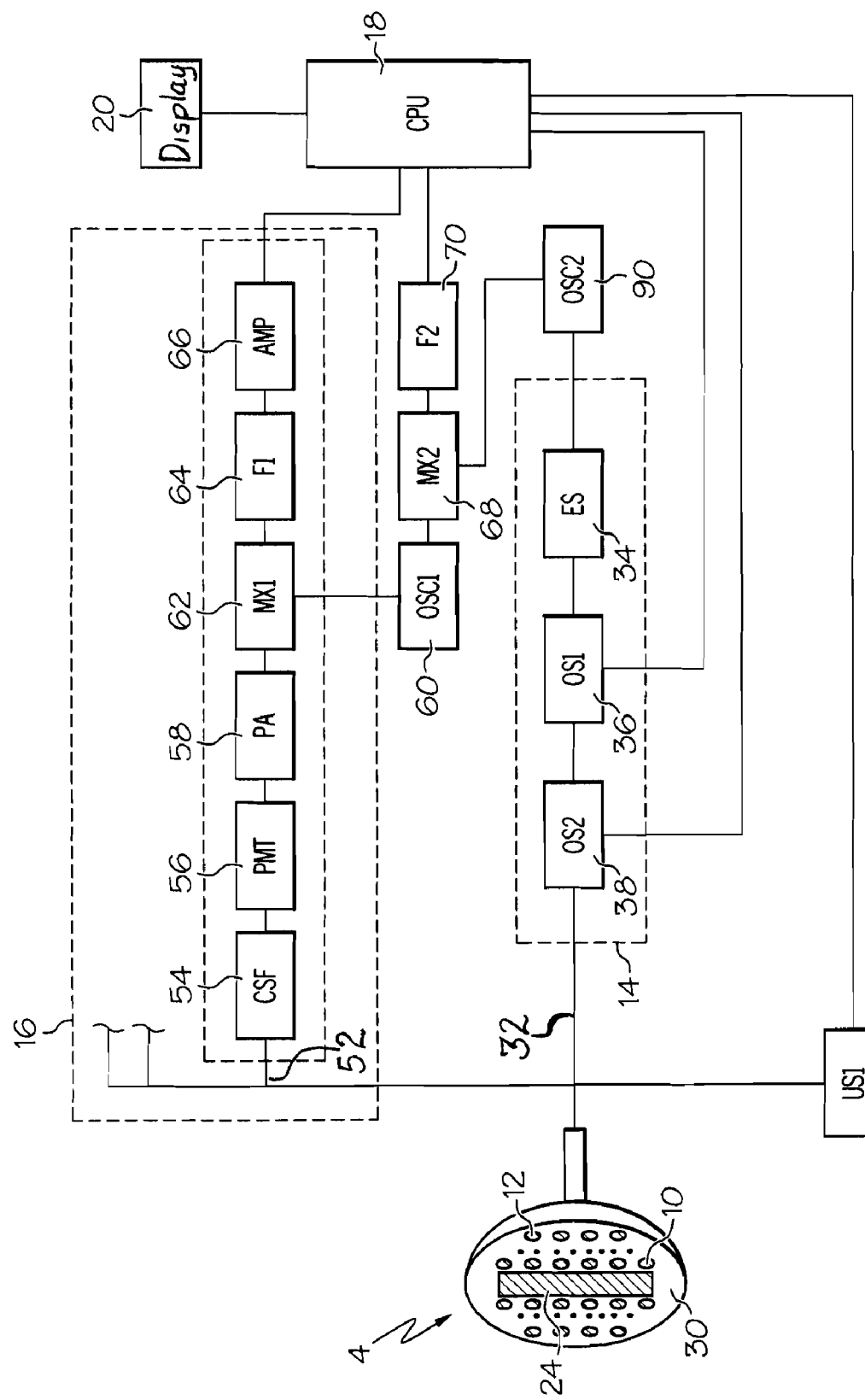
FIG. 3 is an exemplary imaging system.

Referring now to FIG. 3, an exemplary embodiment of an imaging system 200 is illustrated. The imaging system 200 comprises a probe 4 having nine first emitters 10 operably connected to a source circuit 14 via optical fibers 32. The source circuit 14 comprises an excitation source (ES) 34 that is optically connected to a primary optical switch (OS1) 36. The excitation source (ES) 34 comprises multiple excitation elements therein (not shown), such as pigtailed laser diodes capable of emitting near-infrared radiation at 660 nm and near-infrared radiation at 780 nm and 830 nm (e.g., commercially available from Thorlabs Inc.) that is modulated at a predetermined frequency (e.g., 140.00 MHz) by an oscillator (OSC2) 90, which is connected thereto.

The primary optical switch (OS1) 36 is capable of selectively connecting the emissions from any of the excitation elements, or any combination of excitation elements, to a secondary optical switch (OS2) 38 (e.g., commercially available from Piezosystem Jena Inc.). The secondary optical switch (OS2) 38 is capable of selectively directing the emissions from the primary optical switch (OS1) 36 connected to any combination of the nine emitters 10 via, hence allowing the emission of radiation through the emitters 10 selected. The primary optical switch (OS1) 36 and the secondary optical switch (OS2) 38 are connected in operable communication with, and controlled by, CPU 18.

The ten first detectors 12 on the probe 4 are operably connected to the detector circuit 16 via optical fibers 52. The detector circuit 16 comprises detector sub-circuits 54 for each first detector 12 and optically connected thereto via portions of optical fibers 52. Each detector sub-circuit 54 comprises a collimating system and filter (CSF) 54, which is capable of receiving an optical signal (e.g., light) from a first detector 12, collimating the optical signal, and optionally filtering the optical signal to a specific desired frequency range. The optical signal emitted from the collimating system and filter (CSF) 54 is then directed upon photomultiplier tube (PMT) 56 (e.g., commercially available from Hamamatsu Inc.) and converted into a voltage, which is subsequently amplified by pre-amp (PA) 58 (e.g., by about 40 mV). The resulting voltage is mixed with an output carrier signal having a predetermined frequency (e.g., 140.02 MHz) by a local oscillator (OSC1) 60 that is connected in electrical communication with the voltage via mixer 62. The heterodyned signals output by mixer 62 are filtered by a narrowband filters (F1) 64 and further amplified (e.g., by 30 dB) by amplifier (AMP) 66. The amplified signals are then sampled at a predetermined frequency (e.g., 250 KHz) by an analog to digital conversion (A/D) board inside the CPU 18. The signals output by the oscillator (OSC1) 60 are directly mixed with the output of oscillator (OSC2) 90 by mixer 68 to produce a reference signal (e.g., a 20 KHz reference signal). The 20 kHz reference signal is then filtered by a narrowband filter 70 (e.g., 20 KHz) and provided as input to the CPU 18.

The digital co-registered ultrasound images of a commercial ultrasound system are acquired from the image capture card installed in the CPU 18. The images are displayed on the CPU monitor and segmented either by imagers or physicians to provide the region of interest for diffusive optical tomography (DOT) and/or fluorescent diffusive optical tomography (FDOT).

The imaging system 200 is capable of diffusive optical tomography (DOT), fluorescent diffusive optical tomography (FDOT) and ultrasound functions. These imaging techniques are employed to provide structural information (e.g., size, position, and so forth), as well as functional information (e.g., fluorophore concentration) in the form of digital images of a fluorescing target (e.g., an inclusion) within a turbid medium that can be viewed on a display 20. The methods for imaging employed herein are conducted in three main steps, the first is the location and size of the inclusion 8 using ultrasound, the second is the estimation of the structural parameters of the inclusion 8, and the third is the estimation of the functional parameters of the inclusion 8.

In the first step, the use of real time co-registered ultrasound provides initial guidance on the location of the inclusion and its general size. The second and third steps are enabled by the discovery that the ratio of the fluorescence signals excited by a single first emitter 10 and received by two detectors 12 is largely dependent upon the structural parameters of the inclusion 8 when the fluorescence of the background fluorophore can be subtracted from the fluorescence measurements or the uptake of fluorophore into the inclusion 8 is about ideal (e.g., there is no excess fluorophore surrounding the inclusion 8). This discovery therefore enables the structure parameters to be estimated, which in turn is utilized to estimate the functional parameters of an inclusion 8.

The same method described above can be used to estimate the structural parameters using optical measurements from near infrared sources instead of fluorescence measurements, such as signals received from sources emitting near-infrared radiation at about 780 nm or about 830 nm.

Figure 4:
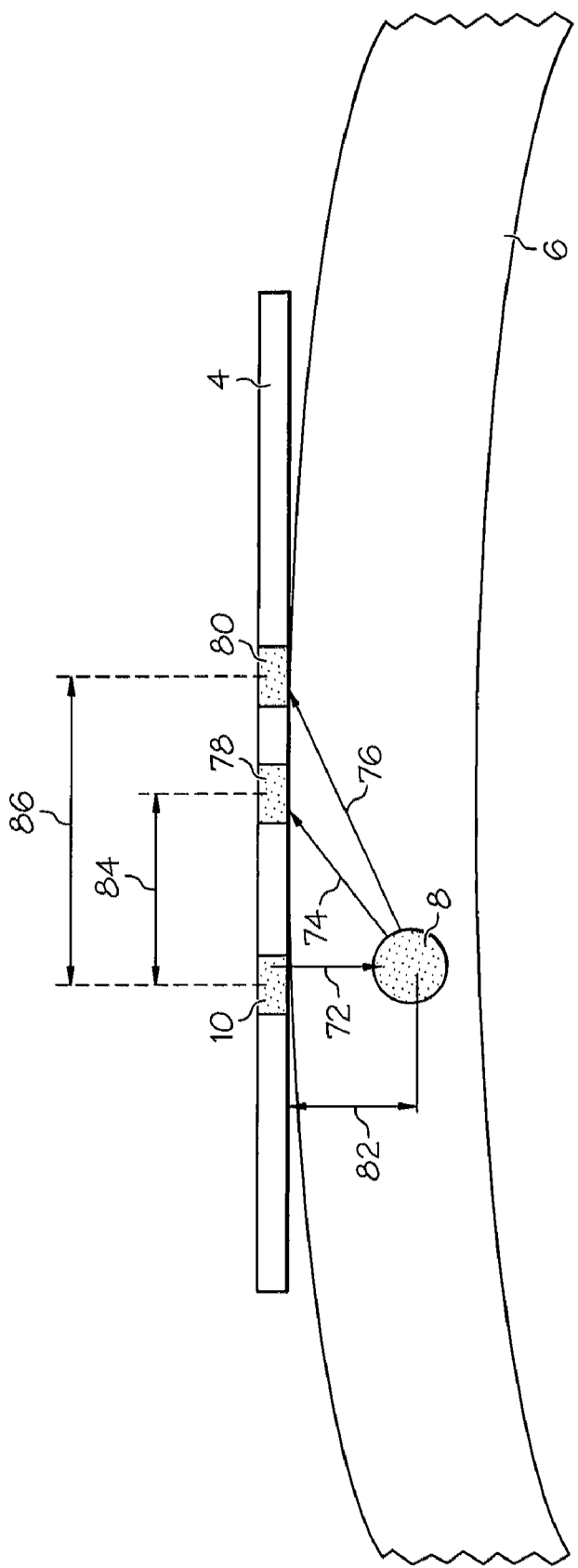
FIG. 4 is an exemplary illustration of the emission and detection of radiation using one emitter and two detectors.

In FIG. 4, an exemplary illustration of the emission and detection of radiation using one first emitter 10 and two first detectors 12. To be more specific, first emitter 10 emits radiation 72 through tissue 6 upon an inclusion 8 disposed a distance 82 from the first emitter 10. Fluorophores within the inclusion 8 are excited by the radiation 72 and fluoresce in the form of fluorescence signals 74 and 76, which are detected by a first detector 78 and a second detector 80 that are disposed a distance 84 and a distance 86 from the first emitter 10, respectively. The fluorophores can be disposed within the inclusion 8 via the injection of a fluorophore dye, such as Cy5.5 and the like. This method of measurement is employed to estimate the structural parameters of the inclusion 8 using the first algorithm depicted in the FIG. 5.

First Algorithm

Figure 5:
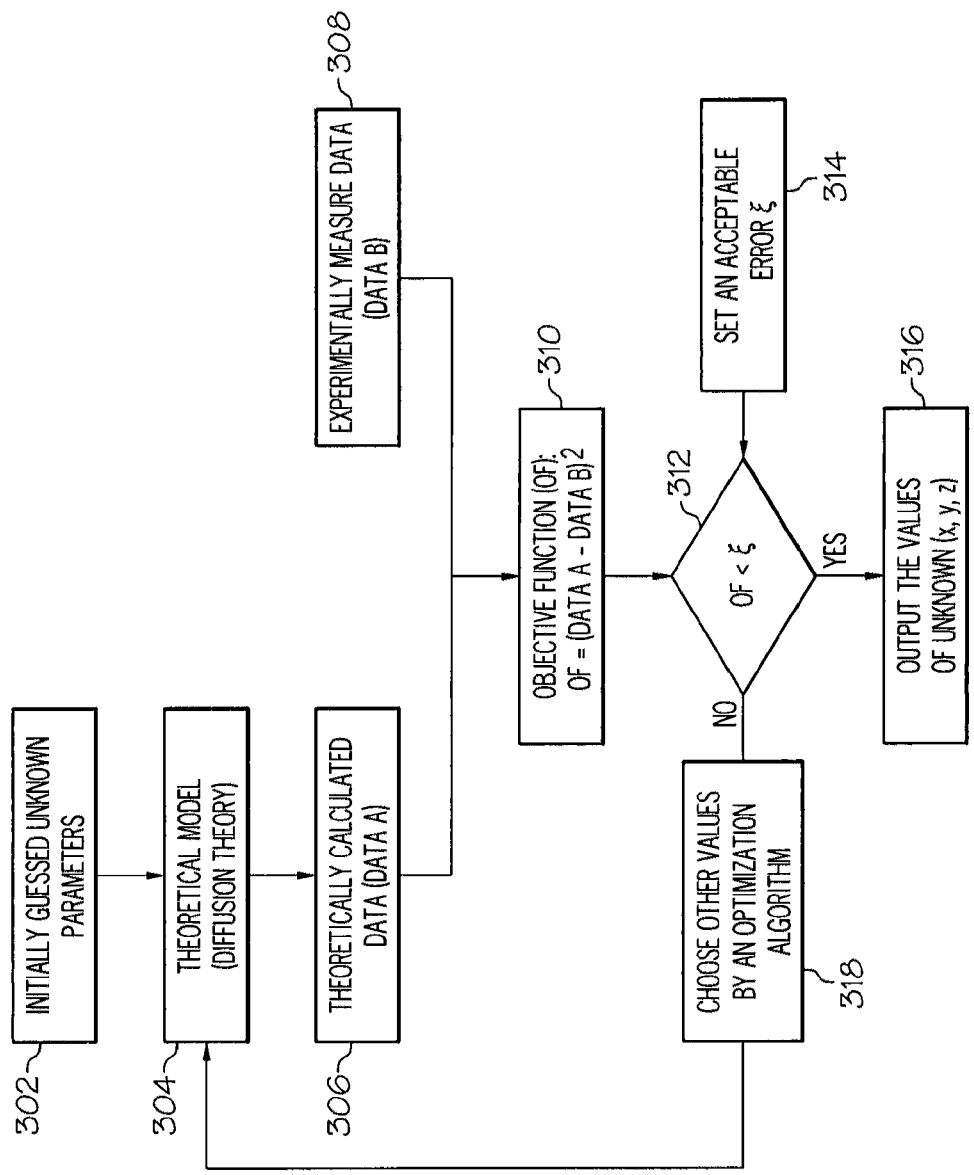
FIG. 5 is an exemplary flowchart illustrating an exemplary process for reconstructing structural parameters utilizing diffusion theory.

In FIG. 5, a flowchart illustrates an exemplary process for reconstructing structural parameters utilizing diffusion theory (as discussed above). The first step 302 of the process is locating the position (in X, Y, and Z coordinates) and the radius ($\alpha$) of the inclusion 8. Once complete, the variables needed for estimating an inclusion's structural parameters using equations 3-9 (detailed below in the second Algorithm) are either input by the user or assigned by the CPU 18 in step 304. The CPU 18 then calculates the theoretically calculated data (Data A) utilizing the diffusion theory equations 3-9 as indicated by step 306. In the step 308, experimentally measured data (Data B), which is calculated from amplitude ratios (R) and phase differences ($\Delta\psi$) is then compared to the theoretically calculated data (Data A) via an objective function, wherein the experimentally measured data (Data B) is generated at any point prior to this comparison (e.g., simultaneous with the calculation of the theoretically calculated data (Data A)). In the step 310, if the objective function is less than an acceptable error ($\epsilon$) (step 314 and step 312), the unknown values (X, Y, and Z coordinates and the radius ($\alpha$) of the inclusion 8) are output as indicated in step 316. If the objective function is not less than an acceptable error ($\epsilon$), other values of (X, Y, Z and $\alpha$) are chosen via an optimization algorithm (e.g., Simplex Down-Hill Technique) and utilized by the CPU 18 to calculate another set of theoretically calculated data (Data A) utilizing the diffusion theory equations 3-9, and the process is repeated until the objective function is less than an acceptable error ($\epsilon$), at which point the unknown values (X, Y, Z and $\alpha$) are output (step 318). The acceptable error for the objective function is generally less than 25%, specifically less than 20%, more specifically less than 15%, more specifically less than 10%, and more specifically less than 5% between the theoretically calculated data and the experimentally calculated data.

Second Algorithm

The structural parameters of an inclusion 8 are defined as the central position of the inclusion 8 (in X, Y, and Z coordinates) and the radius of the inclusion 8. To estimate the structural parameters of the inclusion 8, a fluorescent diffusive optical tomography method is employed, wherein diffusion theory teaches that fluorophores excited by a point source located at $r_s$ (the position of the first emitter 10) and detected by a detector located at $r_D$ (the position of the first detector 12) can be expressed as:

$$\phi^{fl}(r_S, r_D) = \frac{S_0}{4\pi D_{ex} D_{fl}} \frac{\Lambda\varepsilon}{(1-i\omega\tau)} \int_\Omega G_{ex}(r_S, r) G_{fl}(r, r_D) N \, dr^3, \quad (1)$$

wherein r is a spatial variable, $\Omega$ is the target region where the fluorophore is located, $S_0$ is the source strength, and D is the diffusion coefficient. The subscript "ex" indicates the variable is measured at the excitation wavelength, and the subscript "fl" indicates that the variable is measured at the emission wavelength. The variables $\Lambda$, $\tau$, and $\epsilon$ are the quantum yield, lifetime, and extinction coefficient of the fluorophore, respectively. G is a Green's function, which is a mathematic function describing the distribution of photons generated by a point light source in a highly scattering medium with infinite geometry. $N_{(r)}$ is the fluorophore concentration.

With reference now to the FIG. 4, the ratio of the fluorescence detected at the first detector 78 and the second detector 80 can be obtained using the formula, $$\frac{\phi^{fl}(r_{S1}, r_{D2})}{\phi^{fl}(r_{S1}, r_{D1})} = \frac{\int_\Omega G_{ex}(r_{S1}, r) G_{fl}(r, r_{D2}) N(r) \, dr^3}{\int_\Omega G_{ex}(r_{S1}, r) G_{fl}(r, r_{D1}) N(r) \, dr^3}, \quad (2)$$

wherein the difference between the numerator and the denominator is the term $G_{fl}$ (Green's Function of the emission wavelength), which factors in the positions of the two detectors employed. Therefore, the ratio of the fluorescence is mainly dependent on $G_{fl}$ rather than $G_{ex}$ and $N_{(r)}$. Therefore, the amplitude ratio (R), and the phase of the ratio ($\Delta\psi$), can be written as:

$$R = \left| \frac{\phi^{fl}(r_{S1}, r_{D2})}{\phi^{fl}(r_{S1}, r_{D1})} \right|, \text{ and,} \quad (3)$$

$$\Delta\Psi = \text{phase}\left[ \frac{\phi^{fl}(r_{S1}, r_{D2})}{\phi^{fl}(r_{S1}, r_{D1})} \right]. \quad (4)$$

When a spherical fluorescing target with a radius $\alpha$ is embedded into a highly scattering medium with an infinite geometry, the fluorescence detected at $r_d$ and excited by a point source at $r_s$ with a modulation frequency $\omega$ can expressed as;

$$\phi^{fl}(r_s, r_d) = \phi_{out}^{fl}(r_s, r_d) + \phi_{in}^{fl}(r_s, r, r_d), \quad (5)$$

wherein, $$\phi_{out}^{fl}(r_s, r_d) = \frac{S_0}{D_{ex} D_{fl}} \frac{\Lambda\sigma N_{bg}}{(1-i\omega\tau)} \frac{1}{4\pi} \quad (6)$$

$$\frac{1}{(k_{ex}^2 - k_{fl}^2)} \times [(G_{ex}(r_s, r_d) - G_{fl}(r_s, r_d))], \text{ and,}$$

$$\phi_{in}^{fl}(r_s, r, r_d) = S_0 \frac{\Lambda\sigma N_{in}}{1-i\omega\tau} \frac{\alpha^2}{k_{in\_ex}^2 - k_{in\_fl}^2} \times \quad (7)$$

$$\sum_{lm} \{[k_{in\_fl} j_l(k_{in\_ex}\alpha) j'_l(k_{in\_fl}\alpha) - k_{in\_ex} j'_l(k_{in\_ex}\alpha) j_l(k_{in\_fl}\alpha)] \times R_l^{ex}$$

$$R_l^{fl} h_l^{(1)}(k_{out\_fl}|r_d - r|) h_l^{(1)}(k_{out\_ex}|r_s - r|) Y_{lm}(\Omega_{d,r}) Y_{lm}^*(\Omega_{s,r})\},$$

$$G_{ex(fl)}(r_s, r_d) = \frac{\exp(ik_{ex(fl)}|r_s - r_d|)}{|r_s - r_d|}, \text{ and,} \quad (8)$$

$$k_{ex(fl)} = \sqrt{3\mu'_{s\_ex(fl)}(-\mu_{a\_ex(fl)} + i\omega/v)}, \quad (9)$$

wherein the subscripts "in" and "out", denote the inside and outside of the spherical inclusion, respectively. The subscript "ex" indicates the variable is measured at the excitation wavelength and "fl" indicates that the variable is measured at the emission wavelength. Further, k is the wave vector, $N_{bg}$ and $N_{in}$ are the concentrations of fluorophore in the background and the inclusion, respectively. $h_l^{(1)}$ and $j_l$ are Spherical Hankel functions of the first kind and Spherical Bessel functions, respectively. $h'_l^{(1)}$ are $j'_l$ are the first order derivative of $h_l^{(1)}$ and $j_l$, respectively. $Y_{lm}$ and $Y^*_{lm}$ are Spherical Harmonics, and its complex conjugate, respectively. $R_l^{ex}$ and $R_l^{fl}$ were two complex functions defined by X. Remaining parameters are described in reference to equation 1.

Based on equations 6-9, extrapolated boundary conditions, and assuming a semi-infinite geometry (e.g., tissue 6), the amplitude and phase of the fluorescence photon density wave at any position can be obtained from equation (5). Therefore the amplitude ratio R and phase difference $\Delta\psi$ at any two positions can be calculated as functions of the target depth (Z) and radius (α) using equations 3 and 4.

Figure 6:
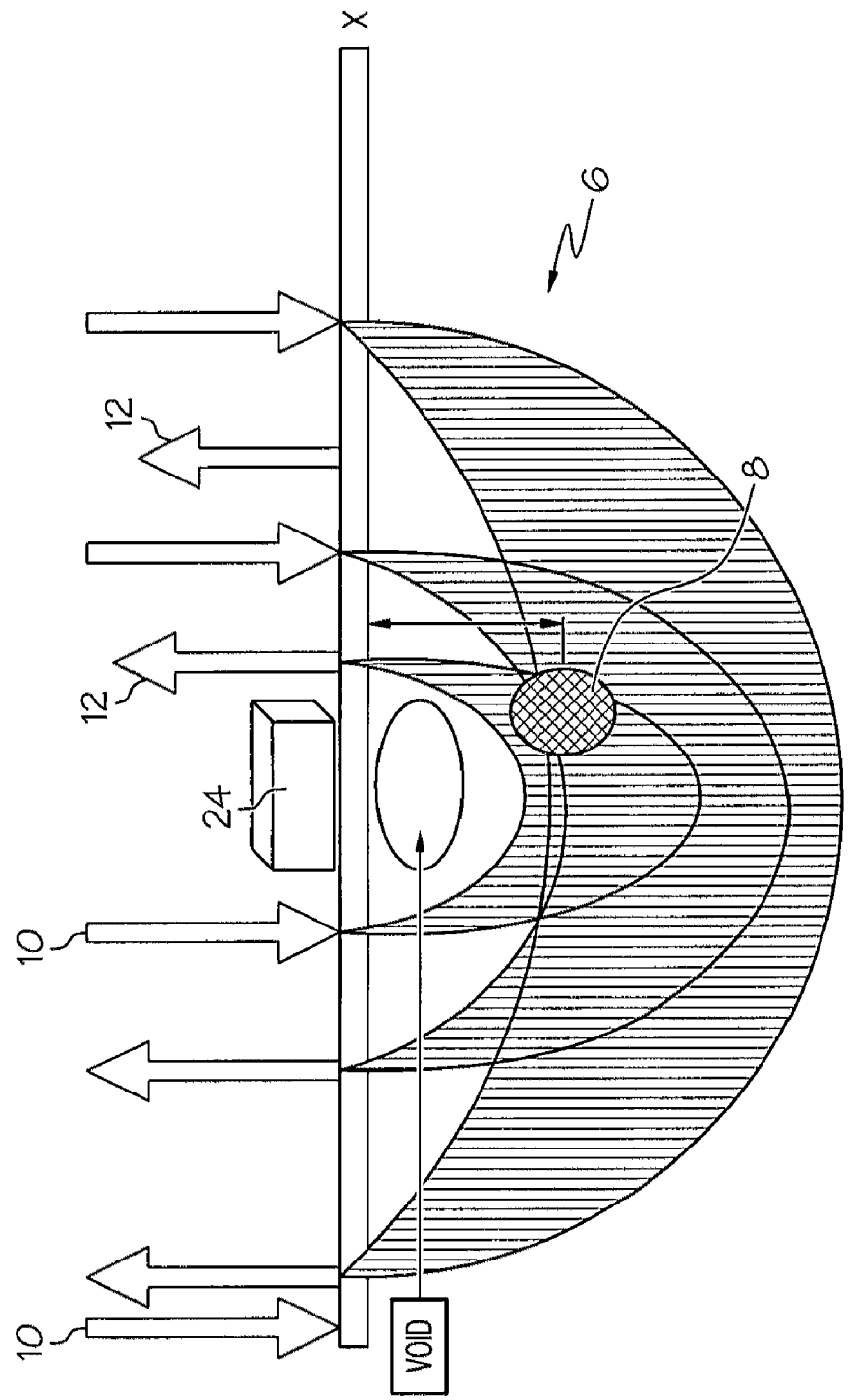
FIG. 6 is an exemplary depiction of the use of ultrasound and light for the detection of shallow inclusions, when the emitters are aligned to be perpendicular to the surface of the tissue.

FIG. 6 illustrates one exemplary approach to ultrasound-guided fluorescence imaging approach. As can be seen in the FIG. 6, the optical energy is introduced into the tissue by a first emitter 10 at an angle that is relatively perpendicular to the surface of the tissue. However, the light (e.g., optical, near-infrared or near ultraviolet) travels a curved, cresent-like path in the tissue. The minimum separated distance between the first emitters 10 and the first detectors 12 determines that the shallowest depth of the maximally sensitive region to an absorbing target is about 1.0 centimeter, which results in low quality images for shallow targets. In the FIG. 6, the ultrasound transducer is located in the center of the probe to provide the size and location of a fluorescence target, the near infrared sources provide excitation wavelength λ1 to illuminate the target, which in turn absorbs the excitation light and generates the fluorescence signals λ2. Multiple emitters and detectors are deployed on a hand-held probe and the fluorescence signals (λ2) are used to form an image of the fluorescence target by using the target size and location provided by ultrasound using the dual-zone-mesh algorithm detailed below. This approach is different from that used by other commercially available methods since it does not depend on optical localization, which, as noted above is not reliable due to intense light scattering in the tissue. The dual-zone-mesh algorithm can be used to optically fine-tune the ultrasonically detected target size and location that provides more accurate target optical properties.

Figure 7:
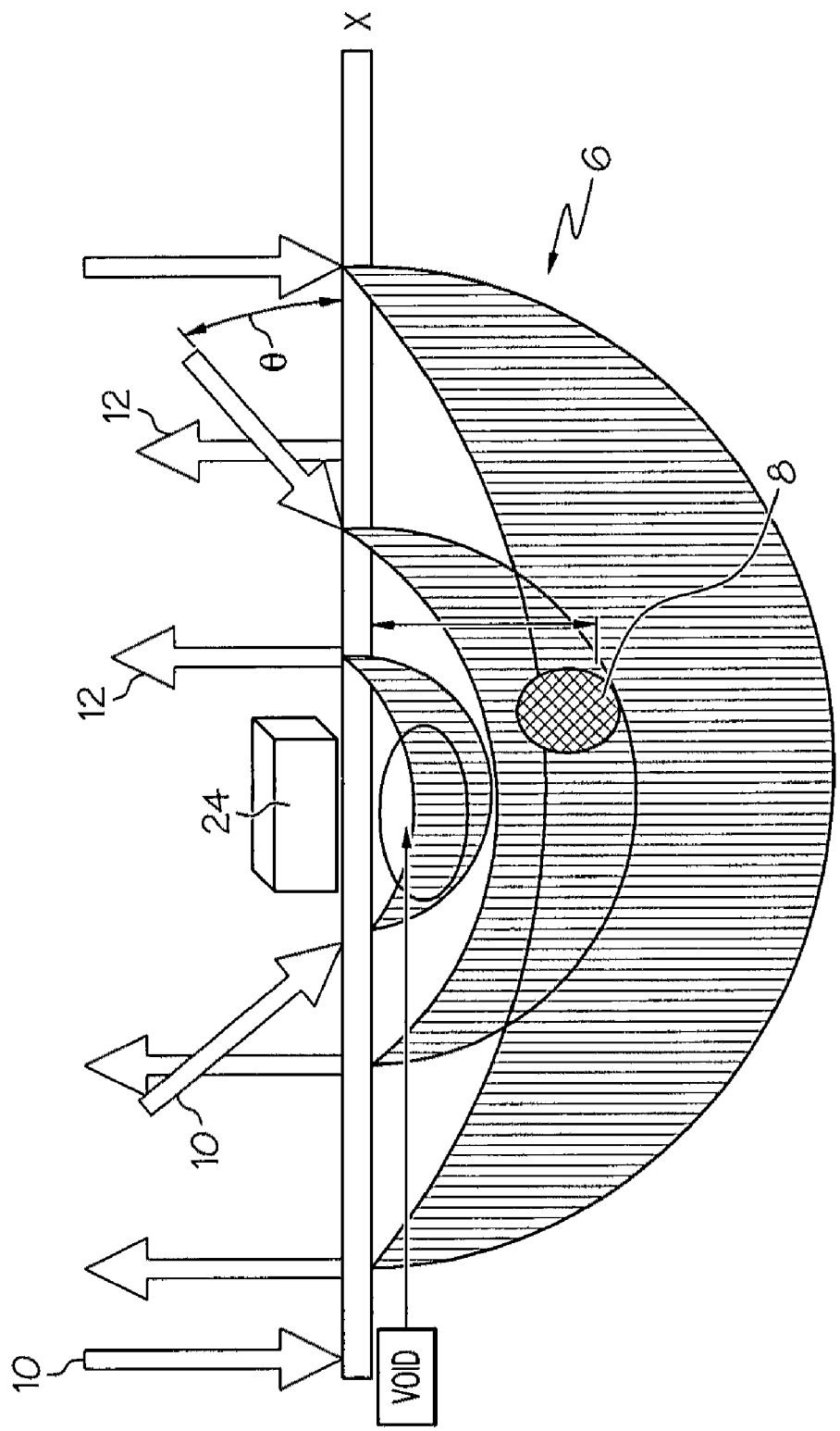
FIG. 7 is an exemplary depiction of the use of ultrasound and light for the detection of shallow inclusions, when the emitters are aligned at an angle of about 20 to about 30 degrees to the surface of the tissue.

In order to overcome the problems of using a light source that is directed perpendicular to the tissue surface and where the first emitters are very closely located to the detectors, FIG. 7 depicts one variation on the FIG. 6. Here, the emitters (e.g., optical, near-infrared or near-ultraviolet) are inclined at an angle θ to the surface of the tissue. The inclination of the emitters improves image quality for shallow targets. The angle θ can be about 10 to about 50 degrees, specifically about 20 to about 30 degrees as shown in FIG. 7.

Figure 8:
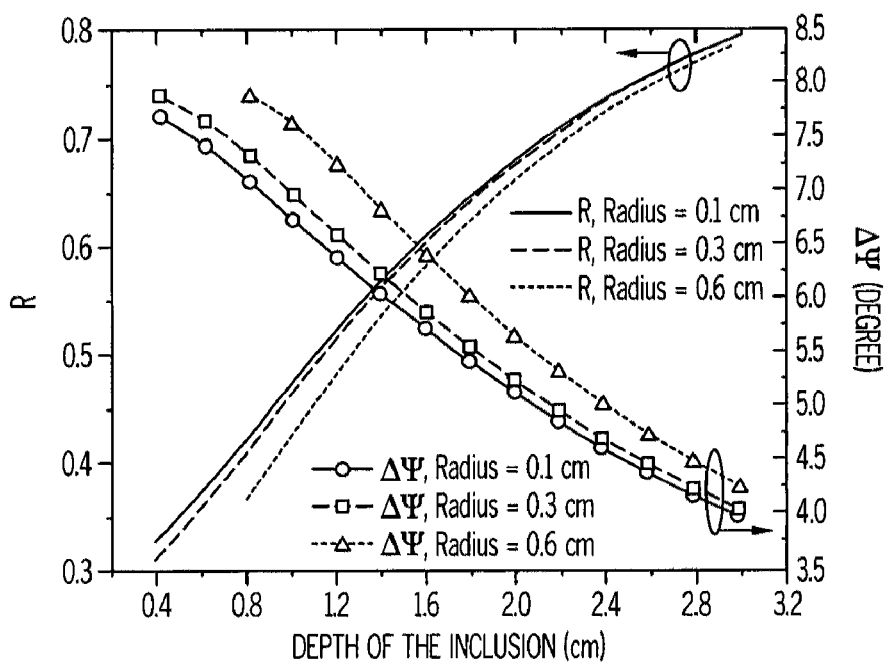
FIG. 8 is an exemplary graph illustrating various amplitude ratios (R) and phase differences ($\Delta\psi$) calculated at various inclusion depths and radii.

FIG. 8 illustrates an exemplary graph that depicts various amplitude ratios (R) and phase differences (Δψ) calculated at various inclusion 8 depths and radii. The calculations assumed a semi-infinite geometry and also assumes that extrapolated boundary conditions were employed. Further, the background parameters utilized in the calculations correspond to a 0.5% intralipid solution, wherein $\mu'_{s\_ex}$=5.0 cm$^{-1}$, $\mu'_{s\_ex}$=4.0 cm$^{-1}$, $\mu_{a\_ex}$=0.009 cm$^{-1}$, $\mu_{a\_fl}$=0.013 cm$^{-1}$. As can be seen in the graph, amplitude ratio (R) and phase differences (Δψ) are largely dependent upon the structural parameters of the inclusion and substantially independent of fluorophore concentration within the inclusion 8.

Figure 9:
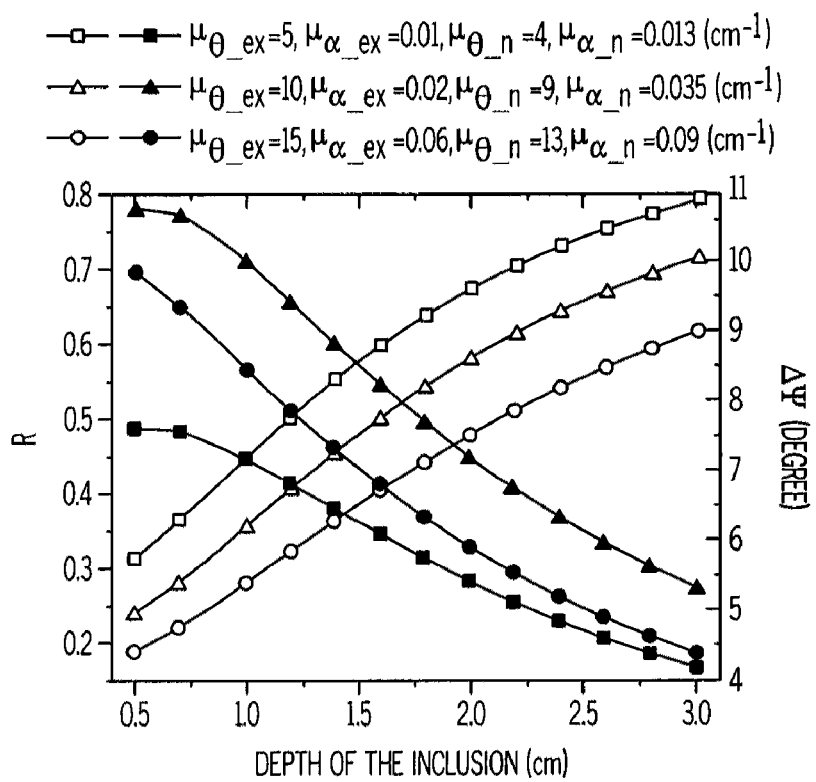
FIG. 9 is an exemplary graph illustrating the effect of variations in background parameters.

Referring now to FIG. 9, an exemplary graph illustrating the effect of variations in background parameters is illustrated. In the graph, various amplitude ratios (R) and phase differences (Δψ) are illustrated that were calculated at various inclusion 8 depths and radii. The calculations assumed a semi-infinite geometry and extrapolated boundary conditions and employed three sets of background parameters. The background parameters were varied to evaluate the effect of these parameters on the resulting amplitude ratios (R) and phase differences (Δψ). As can be seen, the background parameters comprised a first set having $\mu_{s\_ex}$=5.0, $\mu_{s\_fl}$=4.0, $\mu_{a\_ex}$=0.01, $\mu_{a\_fl}$=0.013, a second set having $\mu_{s\_ex}$=10.0, $\mu_{s\_fl}$=9.0, $\mu_{a\_ex}$=0.02, $\mu_{a\_fl}$=0.035, and a third set having $\mu_{s\_ex}$=15.0, $\mu_{s\_fl}$=13.0, $\mu_{a\_ex}$=0.06, $\mu_{a\_fl}$=0.09, wherein all have the units cm$^{-1}$.

As can be seen in FIG. 9, even when these relatively large deviations in background parameters are utilized in the calculations, the resulting amplitude ratio (R) and phase difference (Δψ) also exhibit that these parameters are largely dependent upon the structural parameters of the inclusion and substantially independent of fluorophore concentration within the inclusion 8.

The reconstruction of structural parameters heretofore have been estimated by subtracting, or eliminating, the background fluorescence. In cases wherein the background fluorescence cannot be subtracted, is has been discovered that the effects of the background fluorophore concentration on R is considerably small when the background fluorophore concentration is much lower than that of the inclusion 8. In addition, it has been discovered that the effects of the background concentration on the amplitude ratios (R) is negligible when the position of the detectors are disposed greater than 1.0 cm from the first emitter 10. For example, referring now to FIG. 10, a graph illustrating amplitude ratio (R) with respect to inclusion depth is depicted. A first set of data (shown in solid tick markers) illustrates the resulting amplitude ratios (R) calculated for three background concentrations using a detector set wherein a first detector 78 is disposed 1.0 cm from the first emitter 10 and a second detector 80 that is disposed 1.5 cm from the first emitter 10. A second set of data (shown in unfilled tick markers) illustrates the resulting amplitude ratios (R) calculated for three background concentrations using a detector set wherein a first detector 78 is disposed 1.5 cm from the first emitter 10 and a second detector 80 that is disposed 1.6 cm from the first emitter 10.

Figure 10:
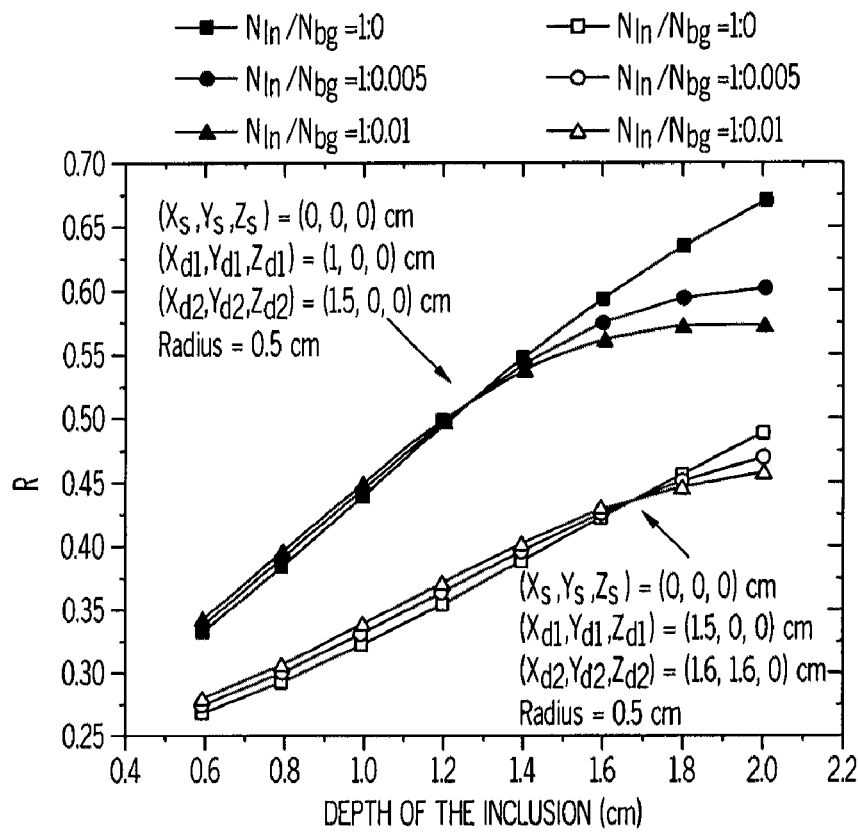
FIG. 10 is an exemplary graph illustrating amplitude ratio (R) with respect to inclusion depth.

As can be derived from FIG. 10, the three plots graphed for each set of data appear to be substantially similar. However, the plots generated from the set of data collected using the first detector 78 at 1.0 cm from the first emitter 10 and the second detector 80 at 1.5 cm from the first emitter 10, substantial divergence is exhibited at inclusion depths greater than about 1.4 cm. However, the data set having the first detector 78 at 1.5 cm from the first emitter 10 and the second detector 80 at 1.6 cm from the first emitter 10 does not exhibit substantiative divergence of the plots above 1.4 cm.

When the background fluorescence cannot be substituted form the target (e.g., inclusion 8), it has been discovered that background concentration exhibits a greater effect on phase difference (Δψ) than amplitude ratio (R). Therefore, in circumstances wherein the background fluorescence cannot be substituted from the target (e.g., inclusion 8), a detector pair can be chosen that is a greater distance from the first emitter 10, and the amplitude ratio (R) can be employed to calculate structural parameters.

Once the estimation of the structural parameters of the inclusion 8 is complete, the functional parameters of the inclusion 8 can be estimated using a normalized Born approximation, which can reconstruct the fluorophore concentration within the inclusion 8. The Born approximation employed can be normalized with a set of measurements to eliminate unknown system parameters, such as source strength and detector gains. In one embodiment, these measurements were gathered from tests on homogeneous fluorescent solutions. The resulting normalized Born equation is, $$\frac{\phi^{fl}}{\phi_0^{fl}} = \sum_j \left( \frac{(k_{ex}^2 - k_{fl}^2)\Delta v}{4\pi N_0^{fl}} \cdot \frac{G_{ex}(r_s, r_j) G_{fl}(r_j, r_d)}{[(G_{ex}(r_s, r_d) - G_{fl}(r_s, r_d))]} \right) \cdot N(r_j), \quad (10)$$

wherein, $$k_{ex(fl)} = \sqrt{(-\mu_{a\_ex(fl)} + i\omega/v)/D_{ex(fl)}} \quad (11)$$

is the wave vector of the diffuse photon density wave at the wavelength of the excitation (emission), $\mu_{a\_ex(fl)}$ is the absorption coefficient of the background medium at the wavelength of the excitation (emission), ω is the modulation frequency of the source, v is the speed of the light in the medium, $\Delta v$ is the volume of each voxel, and $N_0^{fl}$ is the calibrated fluorophore concentration in the homogeneous medium and is used for normalization of the heterogeneous data.

The method employed for reconstructing the fluorescence functional parameters is a dual-zone mesh method, which is employed when the location of the inclusion 8 is known from the procedures described above. Therefore, the structural parameters (e.g., inclusion 8 position (e.g., X, Y, and Z coordinates) and inclusion 8 radius (e.g., volume)) of the inclusion 8 previously estimated are employed to increase the accuracy of the reconstructed functional parameters. Using the estimated parameters, the entire tissue 6 volume is segmented into an inclusion region, L, and a background region, B. Reconstruction is then performed using a finer grid (e.g., 0.1×0.1×0.5 cm) for lesion region L and a relatively coarser grid (e.g., 1.0×1.0×0.5 cm) for the background region B. Equation (10) can then be expressed as a linear matrix equation:

$$[M]_{T \times 1} \times [W_L, W_B]_{T \times N_0} [X_L, X_B]_{N_0 \times 1}, \tag{12}$$

where M corresponds to the value of, $$\frac{\phi^{fl}}{\phi_0^{fl}}, \tag{13}$$

from equation (10), $W_L$ and $W_B$ are weight matrices for the target region and the background region, respectively, having the dimensions of T×NL and T×NB, respectively, wherein T is the total measurement, and NL and NB are the total number of voxels in the target region and the background region, respectively. $N_0$ is equal to NL+NB, and is the total number of voxels. $[X_L]$ and $[X_B]$ are vector representations of the distribution of fluorophore concentration in the target region and the background region, respectively.

As a result of employing the dual-zone mesh method, the total number of voxels with unknown concentration can be maintained on the same scale of the total measurements and the matrix with unknown total fluorophore distribution is appropriately scaled for inversion. Hence, the inverse problem is less underdetermined. In general, only a few iterations are needed for reconstruction to converge to a stable solution. The total least-square method and the conjugate gradient technique are used to iteratively solve equation (11) and yield a detailed distribution of fluorescence concentration of the inclusion 8.

The dual-zone mesh method is also employed for reconstructing the hemoglobin and blood oxygenation saturation functional parameters. In the reconstruction process, the entire tissue volume is segmented based on initial structure estimation into a lesion region, L, and a background region, B. A Born approximation may then be used to relate the scattered field $U'_{sc}(r_{si}, r_{di}, \omega)$ measured at the source-detector pair to absorption variations $\Delta \mu_a(r')$ each volume element of two regions within the sample $$U'_{sc}(r_{si}, r_{di}, \omega) = -\frac{1}{D}\left(\int_L G(r', r_{di})U_{inc}(r', r_{si})\Delta \mu_a(r') d^3 r' + \int_B G(r', r_{di})U_{inc}(r', r_{si})\Delta \mu_a(r') d^3 r' \right) \tag{14}$$

where $U_{inc}(r', r_{si}, \omega)$ and $G(r', r_{di}, \omega)$ are incident wave and Green functions of a semi-infinite geometry, respectively; and $r_{si}$ and $r_{di}$ are source and detector positions. The lesion region L and background region B are then discretized with different voxel sizes (a finer grid for lesion region L and a relatively coarser grid for background region B). The scattered field can then be approximated as $$U'_{sc}(r_{si}, r_{di}, \omega) \approx -\frac{1}{D}\left(\sum_{L_j} G(r_{vj}, r_{di})U_{inc}(r_{vj}, r_{si})\int_j \Delta \mu_a(r') d^3 r' + \sum_{B_k} G(r_{vk}, r_{di})U_{inc}(r_{vk}, r_{si})\int_k \Delta \mu_a(r') d^3 r' \right) \tag{15}$$

where $r_{vj}$ and $r_{vk}$ are centers of voxel j and k in lesion region L and background region B, respectively.

The matrix form of equation (15) is given as, $$[U_{sd}]_{M \times 1} = [W_L, W_B]_{M \times N}[M_L, M_B]^T, \tag{16}$$

where, $$W_L = \left[-\frac{1}{D}G(r_{vj}, r_{di})U_{inc}(r_{vj}, r_{si})\right]_{M \times N_L}, \text{ and,} \tag{17}$$

$$W_B = \left[-\frac{1}{D}G(r_{vk}, r_{di})U_{inc}(r_{vk}, r_{si})\right]_{M \times N_B}, \tag{18}$$

are weight matrixes for lesion and background regions, respectively; and, $$[M_L] = \left[\int_{1_L} \Delta \mu_a(r') d^3 r', \ldots \int_{N_L} \Delta \mu_a(r') d^3 r'\right], \text{ and,} \tag{19}$$

$$[M_B] = \left[\int_{1_B} \Delta \mu_a(r') d^3 r', \ldots \int_{N_B} \Delta \mu_a(r') d^3 r'\right], \tag{20}$$

are total absorption distributions of lesion and background regions, respectively.

Instead of reconstructing $\Delta \mu_a$ distribution directly, as is done in the standard Born approximation, the total absorption distribution M is reconstructed and then the total is divided by different voxel sizes of inclusion 8 and background tissue 6 to obtain the $\Delta \mu_a$ distribution. By choosing a finer grid for lesion and a relatively coarser grid for background tissue, we can maintain the total number of voxels with unknown absorption on the same scale of the total measurements. As a result, the inverse problem is less underdetermined. In addition, since the lesion absorption coefficient is higher than that of background tissue, in general, the total absorption of the lesion over a smaller voxel is on the same scale of total absorption of the background over a bigger voxel, therefore the matrix $[M_L, M_B]$ is appropriately scaled for inversion. The reconstruction is formulated as least square problem and the unknown distribution M can be iteratively calculated using conjugate gradient method. The $\Delta \mu_a$ distributions of lesion and background are readily calculated from the total absorption distribution M by dividing M with different voxel sizes. From the $\Delta \mu_a$ distributions, total hemoglobin concentrations and oxygenation saturations can be calculated.

Third Algorithm

In one embodiment, assuming a spherical target is embedded in a semi-infinite turbid medium, we denote its center position with coordinates (X, Y, Z). According to diffusion theory in frequency domain, the scattering photon field caused by this target can be expressed by the following equation (21)

$$U_{sc}(r_s, r_d) = -\int_\Omega U_0(r_s, r)\frac{\Delta\mu_a(r)}{D}G(r, r_d)dr^3 \quad (21)$$

where $r_s$ and $r_d$ are positions of the source and the detector, respectively. r is a spatial variable. $\Omega$ is the volume of the target. $U_0(r_s, r)$ represents the incident photon influence at position r generated from position $r_s$. D is the diffusion coefficient. G is Green's function. $\Delta\mu_a(r)$ is the difference of the absorption coefficient between the target and the background, which is a function of spatial position r. The ratio of the scattering field signals detected at two different positions and generated by one source can be obtained as:

$$\frac{U_{sc}(r_S, r_{d2})}{U_{sc}(r_S, r_{d1})} = \frac{\int_\Omega U_0(r_S, r)\Delta\mu_a(r)G(r, r_{d2})dr^3}{\int_\Omega U_0(r_S, r)\Delta\mu_a(r)G(r, r_{d1})dr^3} \quad (22)$$

In the estimation of the optical structural parameters, we assume that $\Delta\mu_a(r)$ is a constant for a small size target. Therefore, equation (22) is reduced as $$\frac{U_{sc}(r_S, r_{d2})}{U_{sc}(r_S, r_{d1})} = \frac{\int_\Omega U_0(r_S, r)G(r, r_{d2})dr^3}{\int_\Omega U_0(r_S, r)G(r, r_{d1})dr^3}. \quad (23)$$

Equation (23) implies that the ratio of the scattering photon is mainly dependent on the position of the target r if the positions of the source and the detector are fixed. Accordingly, the center positions (X, Y, Z) and target volume $\Omega$ can be extracted by fitting the ratio of the measured data at different positions to equation (23). In the estimation of the structural parameters, an analytical solution of the scattering photon field developed was employed to replace the integral at the right hand side of equation (23) for efficient computation. Because multiple measurements are usually obtained, multiple amplitude ratios and phase differences can be used to robustly recover the center position of the target and the diameter of the target, which is the integral volume. The chi-square ($\chi^2$) fitting technique was adopted. The target center positions X, Y, Z and diameter were recovered by minimizing $\chi^2$, which is performed by using a simple optimization algorithm, Simplex Down-Hill.

EXPERIMENTAL RESULTS

Example 1

A study was conducted wherein a semi-infinite medium was simulated using 0.5% intralipid solution comprising 0.23 μM of a fluorescent dye (e.g., Cy5.5). The solution was disposed in a vessel, and a hollow, transparent cube measuring 0.8×0.8×0.8 cm was filled with the intralipid solution and 5.0 μM of the fluorescent dye (Cy5.5) and submerged in the vessel. The position of the fluorescent cube was controlled using a three dimensionally adjustable micrometer.

Three tests were then conducted to estimate the fluorescent cubes structural parameters and imaging fluorescence concentration. The first set of measurements was made on the 0.5% Intralipid solution without the fluorescent dye or the cube. This data was considered to be the leakage of excitation light from the collimating system and filter 54. The second set of measurements was made on the solution with the 0.23 μM of a fluorescent dye dissolved therein, without submerging the fluorescent cube. This set of was considered to comprise the leakage signals and the fluorescence signal of the background fluorophore. Subtracting the first set of signals from the second set, we obtained the background fluorescence signals that were used to normalize the measurements when the fluorescence target was submerged. In the third set of measurements a fluorescent cube comprising 5.0 μM of a fluorescent dye was submerged in intralipid solution comprising 0.23 μM of the fluorescent dye. This set of data comprised the leakage signals, the fluorescence signals generated from the background fluorophore, and fluorescence signals generated by the fluorophore in the cube.

Next, the leakage of the excitation light was eliminated from the third data set as noise. After subtracting the leakage signals, the remaining signals were used to retrieve the amplitude and phase of fluorescence signal for imaging the fluorophore concentration, and were used to calculate the amplitude ratios R and phase differences $\Delta\psi$ for estimating the structural parameters. The background signals were used for normalization and calibration.

Figure 11:
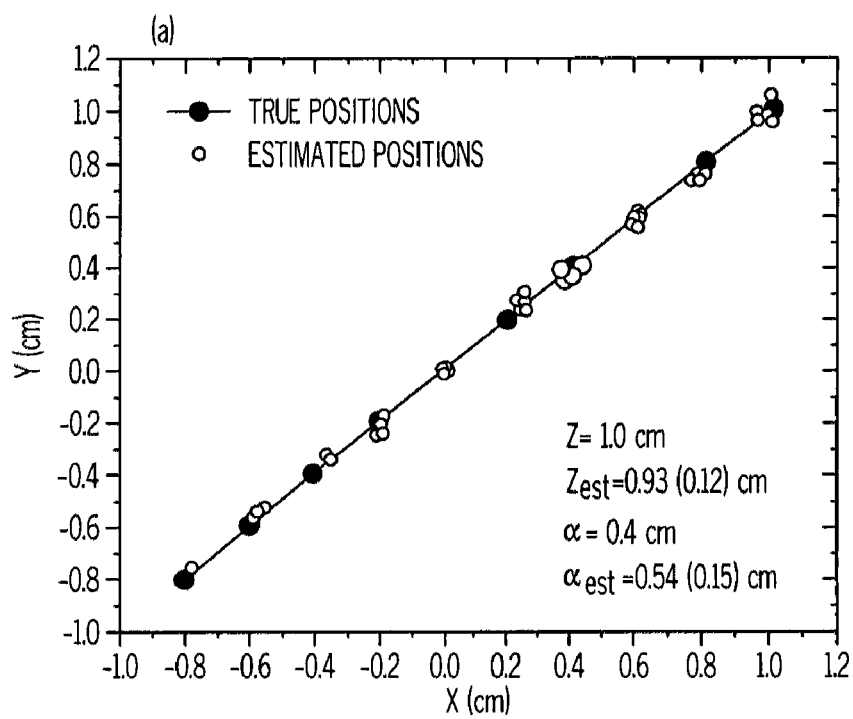
FIG. 11 is an exemplary graph illustrates the estimated position compared to the actual position of the fluorescent cube.

Referring now to FIG. 11, an exemplary graph illustrates the estimated position compared to the actual position of the fluorescent cube as its position was varied within the intralipid solution. As can be seen, the position of the fluorescent cube was estimated with accuracy. This is confirmed with the calculation of the difference (i.e., error) between the mean of the estimated values and the true positions of the fluorescent cube, wherein the error in the X dimension is 0.047 cm, and the error in the Y dimension is 0.065 cm.

Figure 12:
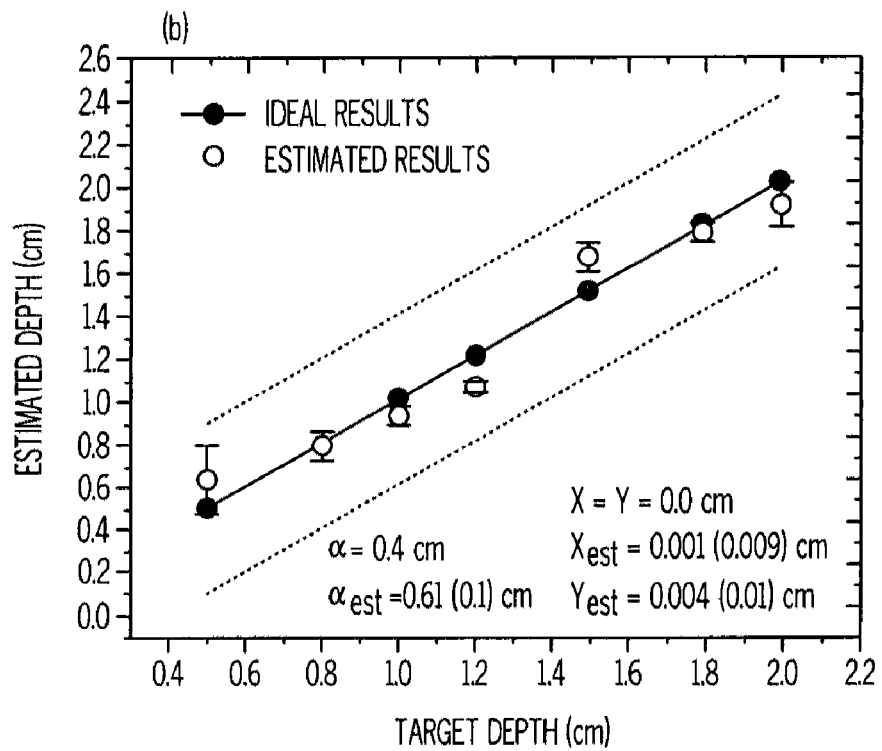
FIG. 12 is an exemplary graph illustrating the estimated depth compared to actual depth of a fluorescent cube in the intralipid solution.

Further, FIG. 12 is an exemplary graph illustrating the estimated depth compared to actual depth of a fluorescent cube in the intralipid solution. In this experiment, the depth of the fluorescent cube was varied, however the X and Y position of the fluorescent cube remained fixed. The dotted lines on the graph indicate the extents of the cubes actual size. As can be seen from the results, the depth of the fluorescent cube was well estimated and well within the actual volume of the fluorescent cube.

Figure 13:
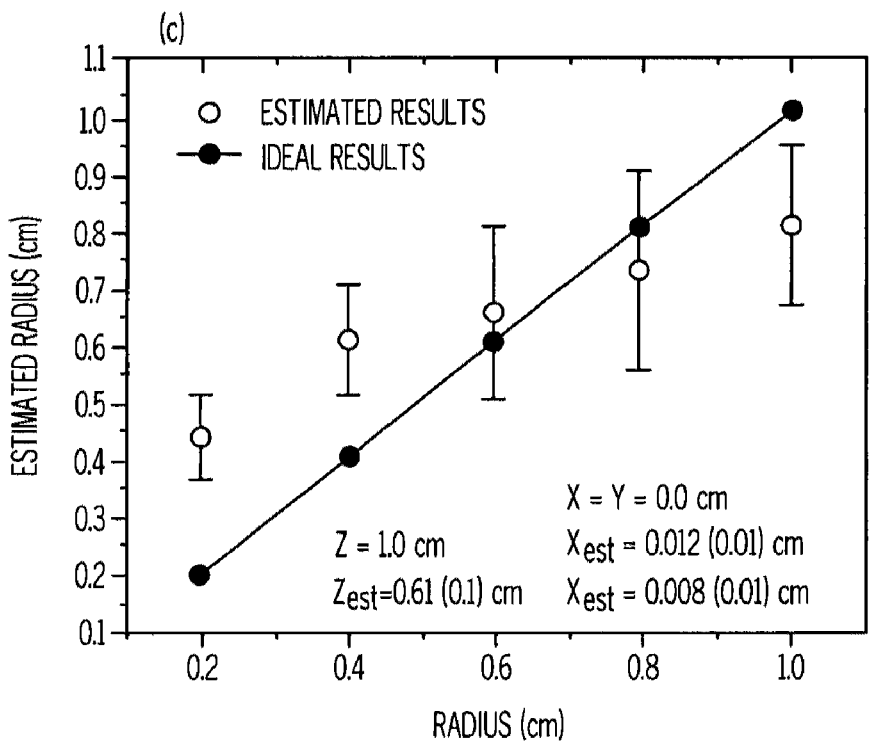
FIG. 13 is an exemplary graph illustrating estimated radius of fluorescent cubes with respect to actual radius.

A test was also conducted to evaluate the imaging systems 2 ability to estimate the radii of various fluorescent cubes within the intralipid solution. Referring now to FIG. 13, a graph illustrates the estimated radius of fluorescent cubes with respect to actual radius. In this experiment the radius α was varied from 0.2 to 1.0 cm while the fluorescent cube's position was fixed. In general, the estimated mean radii have large errors and large standard deviations, which suggests that the estimation accuracy of the radius is lower than those of X, Y, and Z demonstrated in FIGS. 11 and 12. This implies that the correlation of the amplitude ratios R and phase differences $\Delta\psi$ with the target radius is relatively weaker compared with X, Y and Z. However, as will be shown, the reconstruction of the fluorophore concentration only requires an approximate target size because the imaging region is chosen much larger than the true size.

To evaluate the imaging system's 2 ability to reconstruct the functional parameters of an inclusion 8 (e.g., the fluorophore concentration), a hollow, transparent spherical target having a radius of 0.4 cm was filled a 0.5% intralipid solution and a concentration of 5.0 μM of a fluorescent dye (Cy5.5). The sphere was disposed in a semi-infinite medium comprising 0.5% intralipid solution having a concentration of 0.23 μM of a fluorescent dye (Cy5.5) dissolved therein. The parameters of the Cy5.5 fluorescent dye used in the reconstruction were; $\mu_{s\_ex}$=5.0, $\mu_{s\_fl}$=4.0, $\mu_{a\_ex}$=0.009, and $\mu_{a\_fl}$=0.013.

Figure 14:
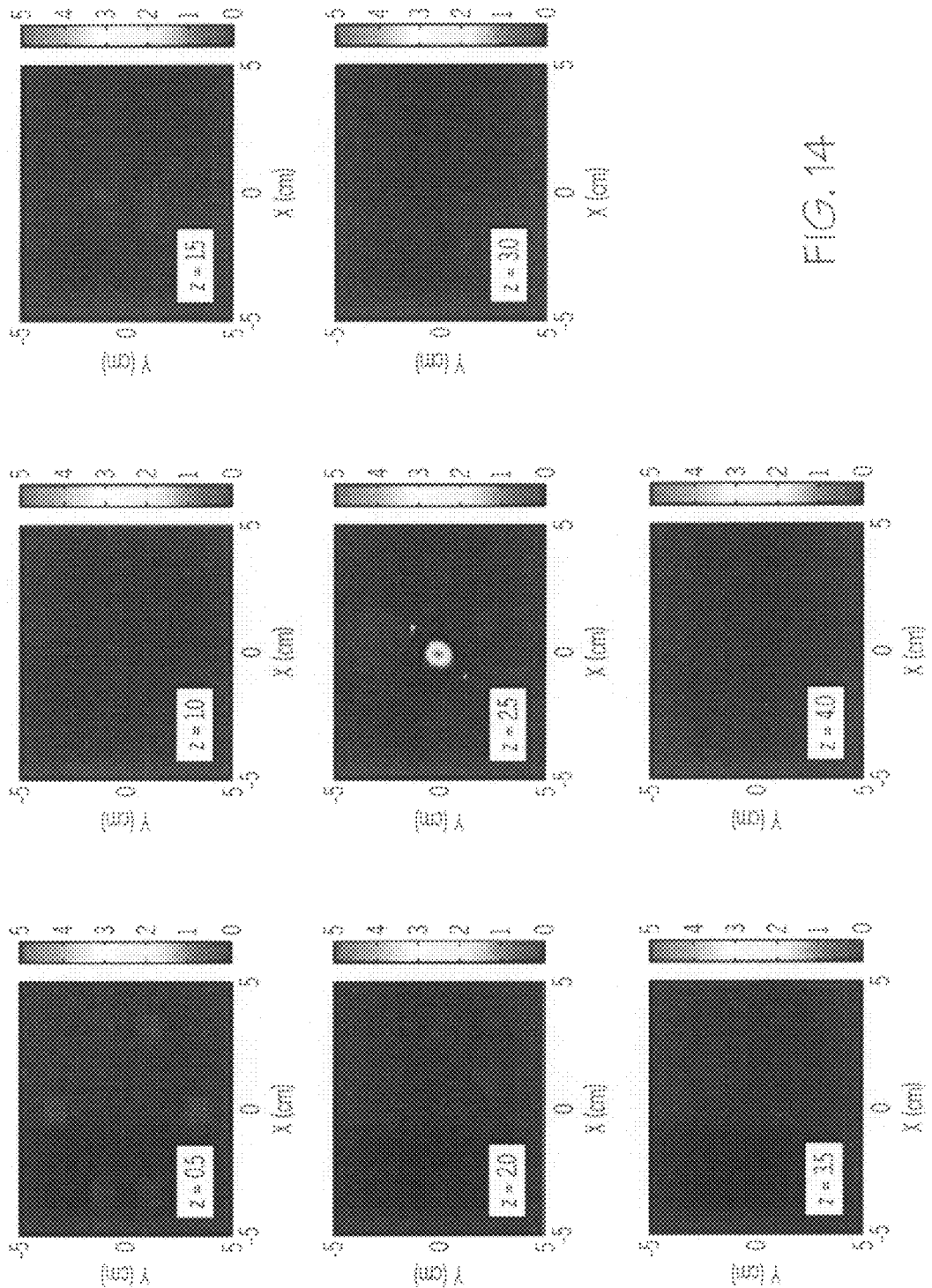
FIG. 14 illustrates exemplary functional reconstruction images in the X-Y plane at different depths for a fluorophore sphere.

The target was located at the center of the imaging region (X=Y=0.0 cm) at a depth was 2.5 cm. Thereafter, the functional reconstruction process was employed to reconstruct images in an X-Y plane at different depths, as illustrated in FIG. 13. FIG. 14 shows eight exemplary functional reconstruction images at different depths for a fluorophore sphere in intralipid solution. As can be seen, the fifth slice reconstructed corresponds to a depth of 2.5 cm, which clearly illustrates the fluorophore filled sphere. Further, it is noted that sphere is not imaged in either the fourth slice having a depth of 2.0 cm or the sixth slice having a depth of 3.0 cm, which is expected since the radius of the target is 0.4 cm, however illustrates the resolution of the reconstruction method.

The percentage of the maximum reconstructed concentration with respect to its true value (5 μM) was 88.54%. The average of the reconstructed values within the full width at half maximum (FWHM) was 67.39%.

The present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Example 2

Figure 15:
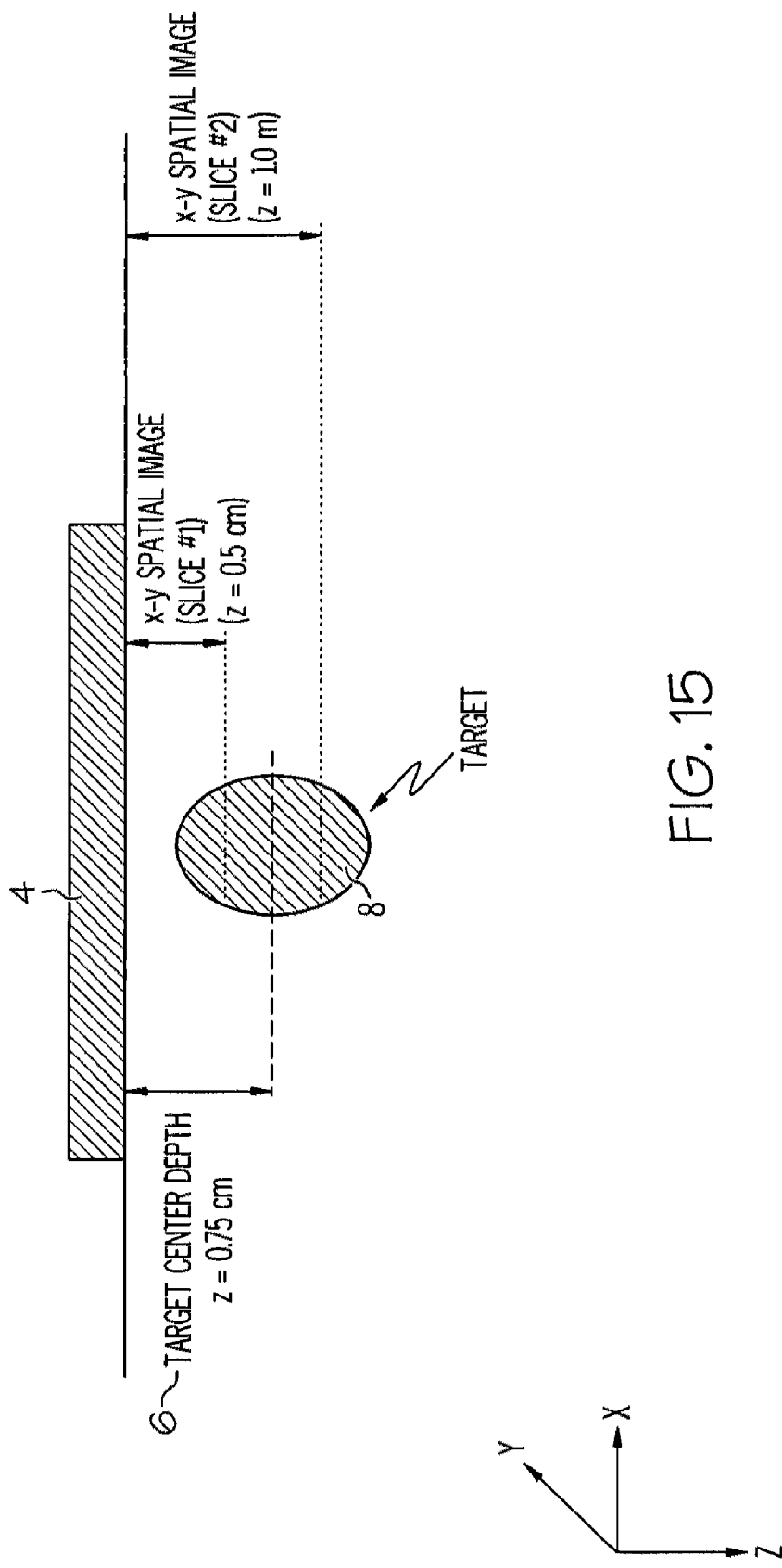
FIG. 15 depicts the experimental set-up for the Example 2.
Figure 16:
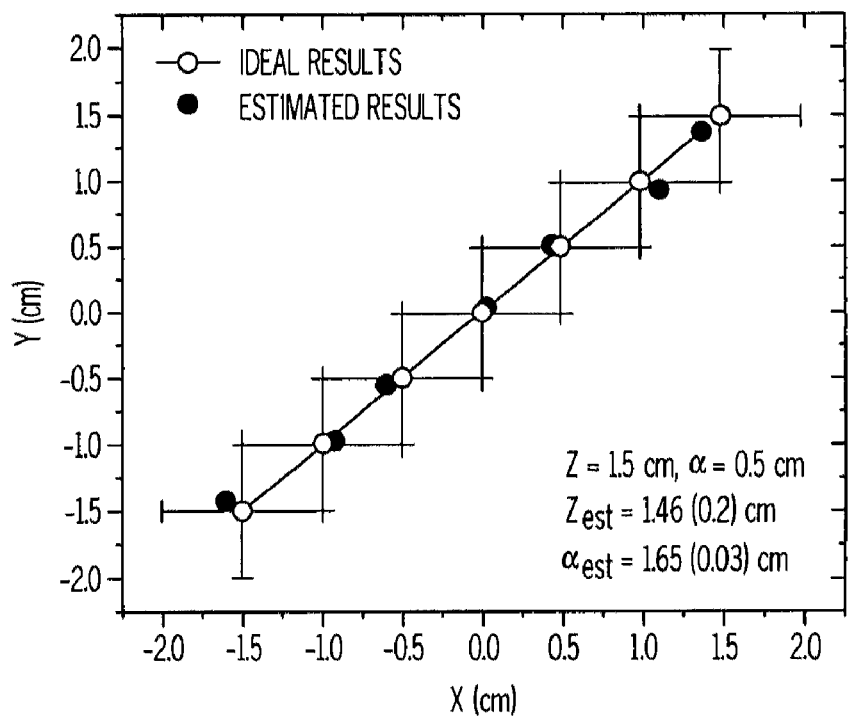
FIG. 16 is a graph depicting the difference between measured and estimated parameters when ultrasound is used in conjunction with DOT in accordance with the fine-tuning first algorithm.

This example was conducted to test the experimental setup depicted in the FIG. 15. It also depicts the difference between using the first algorithm and the third algorithm. FIG. 16 shows the reconstructed X-Y position of the target where the target positions X and Y were simultaneously changed, and the target was controlled at a depth of approximately 1.5 cm. The open circles indicate the measured center positions of the target in the X-Y plane and the bars along X and Y directions denote the radius of the target. The solid circles show the estimated positions. In the FIG. 16, the estimated structural parameters of the spherical target are obtained by using optical imaging method to fine-tune the target parameters. The center positions of the spherical target are in the X-Y plane. The error bars indicate the diameters of the spherical target. The first algorithm was used for the estimation.

Figure 17:
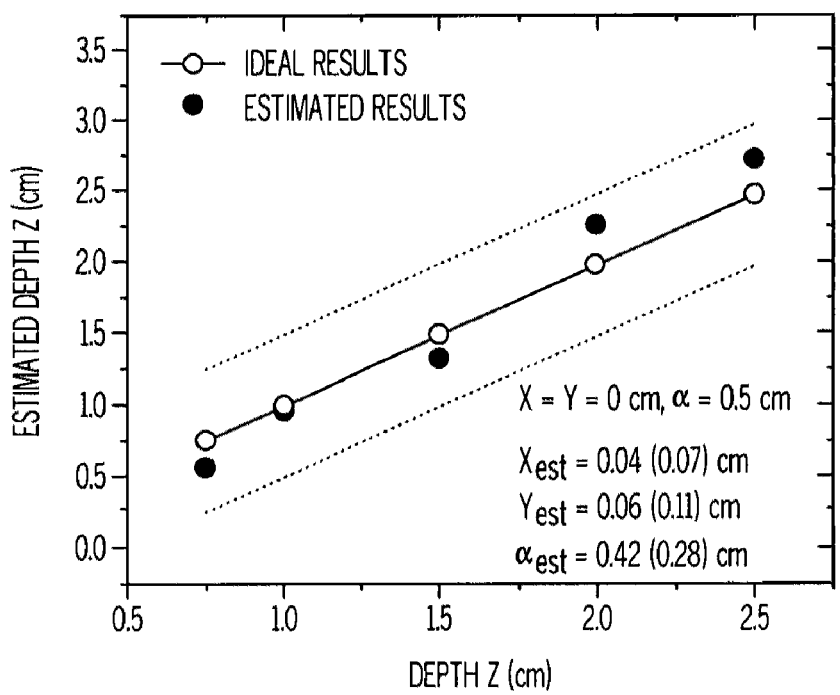
FIG. 17 is a graph depicting the difference between measured and estimated parameters when only ultrasound is used in accordance with the third algorithm which combines the fine tuning first algorithm and the dual-zone mesh reconstruction.

The estimated depth and radius are also shown in FIG. 17 and the numbers in parentheses are the corresponding standard deviations. Here the algorithm was used for estimation of X and Y. It can be seen that the estimated X and Y are considerably close to their expected values. In FIG. 17, we controlled X=0 and Y=0 cm, and varied the depth Z. The dashed line with open circles represents the ideal results and the solid circles show the estimated depths. Two dotted lines indicate the diameter of the target. The target occupies the region within the two dotted lines. It can be seen that all estimated values are within the occupied regions by the target. The center depth of the spherical target in z direction. The open circles represent the expected depths and the solid circles denote the estimated depths. Two dotted lines indicate the diameter of the target, which means that the region between the two dotted lines is occupied by the target.

FIG. 18 provides the reconstructed images of the target where the center position is at X=Y=0 and Z=0.75 cm. The percentages of the maximum reconstructed values relative to the expected value are 94.39% for the slice #1 and 92.66% for the slice #2, respectively. The percentages of the mean values within FWHM are 79.17% for the slice #1 and 78.11% for the slice #2, respectively. Comparing these results with the results reconstructed from the data measured by the US only measurements (Table I), it was found that the fine-tuned optical imaging method could greatly improve the reconstruction accuracy based on the position estimating technique and the dual-zone mesh technique.

TABLE 1

|  | Percentage of reconstructed maximum (%) (Slice #1/ Slice #2) | Percentage of reconstructed averages within FWHM (%) (Slice #1/Slice #2) |
| --- | --- | --- |
| Using the ultrasound and DOT dual-zone mesh (second algorithm) | 34.69/118.68 | 29.06/94.53 |
| Using the ultrasound fine-tune algorithm and DOT dual-zone mesh (third algorithm) | 94.39/92.66 | 79.17/78.11 |

While the invention has been described with reference to a preferred embodiment and various alternative embodiments, it will be understood by those skilled in the art that changes may be made and equivalents may be substituted for elements thereof without departing from the scope of invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for medical imaging using diffusive optical tomography and fluorescent diffusive optical tomography, wherein the method comprises:
    scanning a tissue volume with near-infrared light to obtain structural parameters, wherein the tissue volume includes a biological entity;
    scanning the tissue volume with near-infrared light to obtain optical and fluorescence measurements of the scanned volume;
    segmenting the scanned volume into a first region and a second region; and,
    reconstructing an optical image and a fluorescence image of the scanned volume from the structural parameters and the optical and fluorescence measurements; the reconstructing comprising:
        obtaining structural information and functional information about the biological entity contained in the scanned volume from the structural parameters; wherein structural information about the biological entity contained in the scanned volume is obtained using the equation (2)

$$\frac{\phi^{fl}(r_{S1}, r_{D2})}{\phi^{fl}(r_{S1}, r_{D1})} = \frac{\int_\Omega G_{ex}(r_{S1}, r)G_{fl}(r, r_{D2})N(r)dr^3}{\int_\Omega G_{ex}(r_{S1}, r)G_{fl}(r, r_{D1})N(r)dr^3} \quad (2)$$

where r is a spatial variable, $r_{S1}$ is the position of the first emitter, $r_{D1}$ and $r_{D2}$ are positions of the first and second detector respectively, where the subscript "ex" indicates the variable is measured at the excitation wavelength, and the subscript or superscript "fl" indicates that the variable is measured at the emission wavelength, G is a Green's function, which is a mathematical function describing a distribution of photons generated by a point light source in a highly scattering medium with infinite geometry and $N_{(r)}$ is the fluorophore concentration;

using a model to obtain theoretically calculated data for the structural information and the functional information;

comparing the theoretically calculated data with experimentally measured data to obtain an objective function; and accepting the theoretically calculated data if the objective function lies within an acceptable limit.

2. The method of claim 1, wherein the theoretically calculated data is obtained from an optimization algorithm.

3. The method of claim 1, wherein the structural information comprises the X, Y and Z coordinates of the biological entity.

4. The method of claim 1, wherein the structural information further comprises the radius (α) of the biological entity.

5. The method of claim 1, wherein the functional information comprises amplitude ratios and phase differences between the biological entity and surrounding tissue.

6. The method of claim 1, wherein the theoretically calculated data is optimized using a dual-zone-mesh algorithm.

7. The method of claim 1, wherein the first region consists essentially of a volume of the biological entity.

8. The method of claim 1, wherein the second region comprises the biological entity; the second region encompassing a volume that is larger than the bio logical entity.

9. The method of claim 1, wherein the structural information about the biological entity contained in the scanned volume is obtained using ultrasound.

10. The method of claim 1, wherein structural information and functional information about the biological entity contained in the scanned volume is obtained using a Born approximation.

11. The method of claim 1, wherein structural information about the biological entity contained in the scanned volume is further obtained using equations (1):

$$\phi^{fl}(r_S, r_D) = \frac{S_0}{4\pi D_{ex} D_{fl}} \frac{\Lambda\varepsilon}{(1-i\omega\tau)} \int_\Omega G_{ex}(r_S, r)G_{fl}(r, r_D)N(r)dr^3 \quad (1)$$

where r is a spatial variable, the subscribe "s" indicates the position of the first emitter, while the subscript "D" indicates the position of the first detector respectively $S_0$ is the source strength, and D is the diffusion coefficient, and wherein the subscript "ex" indicates the variable is measured at the excitation wavelength, and the subscript "fl" indicates that the variable is measured at the emission wavelength, where variables Λ, τ, and ε are a quantum yield, lifetime, and extinction coefficient of the fluorophore respectively; G is a Green's function, which is a mathematic function describing a distribution of photons generated by a point light source in a highly scattering medium with semi-infinite and infinite geometry and $N_{(r)}$ is the fluorophore concentration.

12. A method for medical imaging using diffusive optical tomography and fluorescent diffusive optical tomography, wherein the method comprises:

scanning a tissue volume with ultrasound energy to obtain structural parameters;

scanning the tissue volume with near-infrared light to obtain optical and fluorescence measurements of the scanned volume;

segmenting the scanned volume into an inclusion region and a background region; and, reconstructing an optical image and a fluorescence image of at least a portion of the scanned volume from the structural parameters and the optical and fluorescence measurements; the reconstructing comprising:

obtaining structural information and functional information about a biological entity contained in the scanned volume; the structural information obtained from the ultrasound energy;

wherein structural information about the biological entity contained in the scanned volume is obtained using an equation (2)

$$\frac{\phi^{fl}(r_{S1}, r_{D2})}{\phi^{fl}(r_{S1}, r_{D1})} = \frac{\int_\Omega G_{ex}(r_{S1}, r)G_{fl}(r, r_{D2})N(r)dr^3}{\int_\Omega G_{ex}(r_{S1}, r)G_{fl}(r, r_{D1})N(r)dr^3} \quad (2)$$

where r is a spatial variable, $r_{S1}$ is the position of the first emitter, $r_{D1}$ and $r_{D2}$ are positions of the first and second detector respectively, where the subscript "ex" indicates the variable is measured at the excitation wavelength, and the subscript or superscript "fl" indicates that the variable is measured at the emission wavelength, G is a Green's function, which is a mathematical function describing a distribution of photons generated by a point light source in a highly scattering medium with semi-infinite and infinite geometry and $N_{(r)}$ is the fluorophore concentration;

using a model to obtain theoretically calculated data for the structural information and the functional information;

comparing the theoretically calculated data with experimentally measured data to obtain an objective function; and accepting the theoretically calculated data if the objective function lies within an acceptable limit.

13. The method of claim 12, wherein the biological entity comprises a fluorophore.

14. An apparatus for medical imaging using diffusive optical tomography and fluorescent diffusive optical tomography comprising;

a probe comprising a first emitter and a first detector;

the probe comprising a second emitter; the second emitter emitting ultrasound energy;

a source circuit connected in operational communication to the emitter;

a detector circuit connected in operational communication to the detector;

a central processing unit connected to the source circuit and the detector circuit;

a display operably connected to the central processing unit; and, wherein the central processing unit is capable of processing information to provide diffusive optical tomography and fluorescent diffusive optical tomography, wherein the central processing unit is operative to obtain structural information about a biological entity contained in a scanned volume from an equation (2)

$$\frac{\phi^{fl}(r_{S1}, r_{D2})}{\phi^{fl}(r_{S1}, r_{D1})} = \frac{\int_\Omega G_{ex}(r_{S1}, r) G_{fl}(r, r_{D2}) N(r) d r^3}{\int_\Omega G_{ex}(r_{S1}, r) G_{fl}(r, r_{D1}) N(r) d r^3} \quad (2)$$

where r is a spatial variable, $r_{S1}$ is the position of the first emitter, $r_{D1}$ and $r_{D2}$ are positions of the first and second detector respectively, where the subscript "ex" indicates the variable is measured at the excitation wavelength, and the subscript or superscript "fl" indicates that the variable is measured at the emission wavelength, G is a Green's function, which is a mathematical function describing a distribution of photons generated by a point light source in a highly scattering medium with semi-infinite and infinite geometry and $N_{(r)}$ is the fluorophore concentration.

15. The probe of claim 14, wherein information obtained from the ultrasound energy is replaced with information obtained from x-rays, photo acoustic energy or magnetic resonance imaging.

16. The probe of claim 15, wherein information obtained from the ultrasound energy is combined with information obtained from x-rays, photo acoustic energy or magnetic resonance imaging.

17. An apparatus for biological imaging comprising;
a probe comprising an emitter and a detector;
a source circuit connected in operational communication to the emitter;
a detector circuit connected in operational communication to the detector;
a central processing unit connected to the source circuit and the detector circuit;
a display operably connected to the central processing unit; and,
wherein the apparatus is capable of diffusive optical tomography and fluorescent diffusive optical tomography; wherein the central processing unit is operative to obtain structural information about a biological entity contained in a scanned volume from an equation (2)

$$\frac{\phi^{fl}(r_{S1}, r_{D2})}{\phi^{fl}(r_{S1}, r_{D1})} = \frac{\int_\Omega G_{ex}(r_{S1}, r) G_{fl}(r, r_{D2}) N(r) d r^3}{\int_\Omega G_{ex}(r_{S1}, r) G_{fl}(r, r_{D1}) N(r) d r^3} \quad (2)$$

where r is a spatial variable, $r_{S1}$ is the position of the first emitter, $r_{D1}$ and $r_{D2}$ are positions of the first and second detector respectively, where the subscript "ex" indicates the variable is measured at the excitation wavelength, and the subscript or superscript "fl" indicates that the variable is measured at the emission wavelength, G is a Green's function, which is a mathematical function describing a distribution of photons generated by a point light source in a highly scattering medium with semi-infinite and infinite geometry and $N_{(r)}$ is the fluorophore concentration.

* * * * *